(12) United States Patent
Douglas et al.

(10) Patent No.: US 11,113,453 B1
(45) Date of Patent: Sep. 7, 2021

(54) METHOD AND APPARATUS FOR IMPROVED PRESENTATION OF INFORMATION

(71) Applicants: Robert Edwin Douglas, Winter Park, FL (US); David Byron Douglas, Winter Park, FL (US); Kathleen Mary Douglas, Winter Park, FL (US)

(72) Inventors: Robert Edwin Douglas, Winter Park, FL (US); David Byron Douglas, Winter Park, FL (US); Kathleen Mary Douglas, Winter Park, FL (US)

( * ) Notice: Subject to any disclaimer, the term of this patent is extended or adjusted under 35 U.S.C. 154(b) by 0 days.

(21) Appl. No.: 17/187,804

(22) Filed: Feb. 28, 2021

Related U.S. Application Data

(63) Continuation-in-part of application No. 17/138,821, filed on Dec. 30, 2020.

(51) Int. Cl.
| | | |
|---|---|---|
| G06K 9/00 | (2006.01) |
| G06E 1/00 | (2006.01) |
| G06F 40/14 | (2020.01) |
| G06T 11/60 | (2006.01) |
| G06T 11/00 | (2006.01) |
| G06K 9/62 | (2006.01) |
| G06F 40/106 | (2020.01) |
| G06F 3/01 | (2006.01) |

(52) U.S. Cl.
CPC .............. *G06F 40/14* (2020.01); *G06F 3/013* (2013.01); *G06F 40/106* (2020.01); *G06K 9/00315* (2013.01); *G06K 9/00442* (2013.01); *G06K 9/6254* (2013.01); *G06K 9/6256* (2013.01); *G06T 11/001* (2013.01); *G06T 11/60* (2013.01)

(58) Field of Classification Search
USPC ........ 382/100, 103, 106, 112–114, 116, 118, 382/128, 156, 164, 168, 173, 181, 206, 382/214, 243, 254, 275, 276, 286, 291, 382/292, 305; 706/6, 15, 20, 25
See application file for complete search history.

(56) References Cited

U.S. PATENT DOCUMENTS

| | | | | |
|---|---|---|---|---|
| 2016/0301735 A1* | 10/2016 | Lind | ................. | H04M 15/8083 |
| 2018/0121954 A1* | 5/2018 | Jones | ..................... | G06Q 40/02 |
| 2018/0137543 A1* | 5/2018 | Thomas | ............. | G06Q 30/0277 |
| 2019/0347287 A1* | 11/2019 | Crossno | ............. | G06Q 30/0269 |
| 2020/0302029 A1* | 9/2020 | Holm | .................. | G06K 9/6253 |
| 2021/0027868 A1* | 1/2021 | McNeil | .................. | G16H 50/20 |

* cited by examiner

*Primary Examiner* — Seyed H Azarian

(57) ABSTRACT

A method and apparatus comprising generating a dynamic content blocker. An image, which may be comprised of words, symbols and pictures, is segmented into items. Each item is analyzed by an artificial intelligence algorithm. Items can be determined by the AI algorithm to be of non-interest. The dynamic content blocker consists of a blocking image, which is dynamically placed over the items of non-interest, as determined by the AI. If the AI determines that the items are of interest, then these items will remain visible to the user. This will therefore generate a more eye-appealing image for the user and improve the presentation of imagery to a user.

18 Claims, 24 Drawing Sheets

EXAMPLE HOMEPAGE FOR THE MY SITE APPLICATION / WEBSITE HOME PAGE

TYPES OF DATA USED TO TRAIN THE AI ALGORITHM

User inputs:
- Active feedback from user:
  - User clicks on a segmented item (with option to generate manual input of classification) to deliberately train the AI. This could be done via an "of interest" button or an "of non-interest" button.
- Passive feedback from user:
  - User facial expression characterization.
  - User eye tracking
  - Time spent reading the article
  - Whether the article was forwarded to a friend.

Content classification:
- Image analysis
- Symbol analysis
- Semantic analysis
- Sound analysis
- Text appearance analysis

Figure 5

TYPES OF CATEGORIES FOR CLASSIFICATION

- "Of interest" vs. "of non-interest"
- "Of importance" vs. "of non-importance"
- "Makes happier" vs."makes less happy"
- "Motivates" vs. "does not motivate"
- "Likely to be of interest to girlfriend" vs. "not likely to be of interest to girlfriend"
- "Likely to be on bucket list" vs "not likely to be on bucket list"

SEGMENTATION OF THE IMAGE DISPLAYED ON A COMPUTER MONITOR

DYNAMIC CONTENT BLOCKER IMAGE
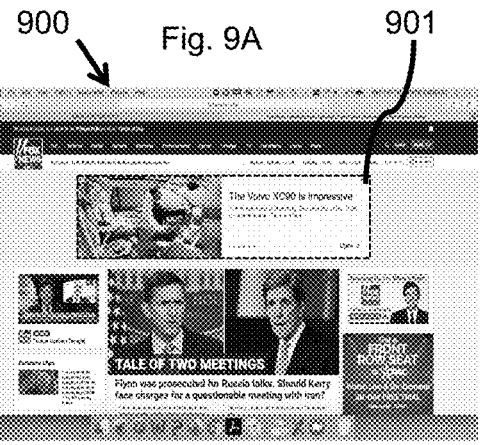
Fig. 9A  900 / 901
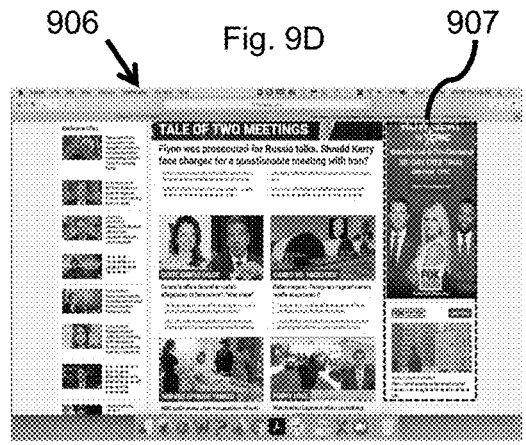
Fig. 9D  906 / 907
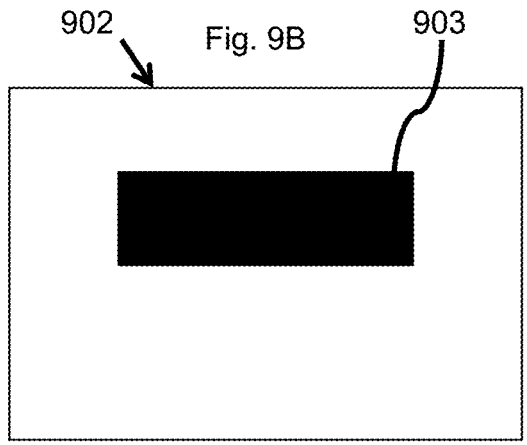
Fig. 9B  902 / 903
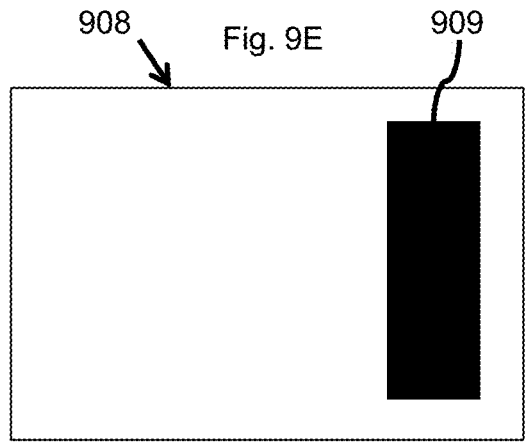
Fig. 9E  908 / 909
Fig. 9C  904 / 905
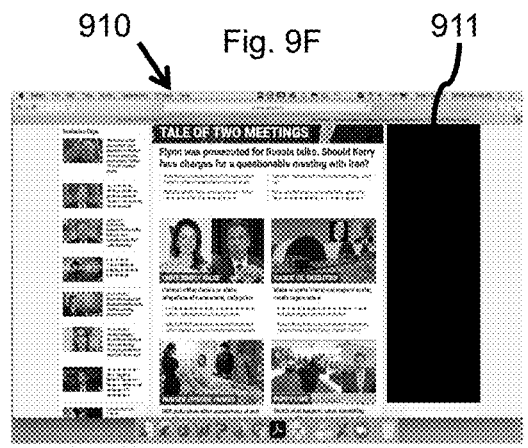
Fig. 9F  910 / 911

DYNAMIC CONTENT BLOCKER: VARIABLE APPEARANCE

GENERATING A PERSONALIZED WEBPAGE WITH RE-ARRANGING AND RESIZING OF "OF INTEREST" ITEMS ONLY

GENERATING A PERSONALIZED, COMPOSITE WEBPAGE WITH RE-ARRANGING AND RESIZING OF "OF INTEREST" ITEMS ONLY

GENERATING A PERSONALIZED, COMPOSITE WEBPAGE WITH RE-ARRANGING AND RESIZING OF "OF INTEREST" ITEMS ONLY

SELECTING A LINK ON A PERSONALIZED, COMPOSITE WEBPAGE

1725

SECONDARY NOTIFICATIONS RELATING INFORMING USER ABOUT DISPLAYED CONTENT

Develop pre-determined criteria wherein predetermined criteria associates content classifications with notifications (sound(s), haptic feedback, visual notification(s))
For example:
- Content in an item is classified as of high interest to a financial investment in a personal stock of a user is associated with a predetermined notification is a "ka-ching" sound
- Content in an item is classified as a exciting sports related content is associated with a predetermined flash of a picture of a baseball over the item
- Content in an item is classified as an exciting event that a user may want to participate in is associated with a haptic feedback notification

1800

Classify content displayed on a monitor
1801

If classified content has an associated notification based on pre-determined criteria, then deliver the notification(s) to the user
For example:
- Content is classified as being related to a personal stock of a user and a a "ka-ching" sound is delivered to a user.
- Content is classified as a exciting sports and a flash of a picture of a baseball over the item is displayed to the user.
- Content is classified as an exciting event that a user may want to participate in and a haptic feedback notification is provided to the user.

EXAMPLE OF HOW CLASSIFIED CONTENT IS DETERMINED TO BE DISPLAYED TO A USER

| Content classification | Filtering status | Predetermined notification |
|---|---|---|
| Sale of sporting equipment | Filtered | None |
| News about COVID-19 | Not filtered | None |
| News about Tom Brady | Not filtered | Provide personalized audio notification |
| Sale at Talbots | Filtered | None |
| MBA recruitment | Filtered | None |
| Precious metal advertisement | Filtered | None |
| Scuba travel | Filtered | None |

Figure 19

ARTIFICIAL INTELLIGENCE FILTERED APPLICATIONS

EXAMPLES OF ARTIFICIAL INTELLIGENCE-FILTERED APPLICATIONS
- Internet searches
- E-mail
- Calendar events
- Games
- Directions
- Dating applications
- Food delivery

Figure 20

METHOD AND APPARATUS FOR IMPROVED PRESENTATION OF INFORMATION

TECHNICAL FIELD

Aspects of this disclosure are generally related to presentation of information to a user.

BACKGROUND

Users work with a variety of websites and applications on mobile phones, tablets and laptop computers.

SUMMARY

All examples, aspects and features mentioned in this document can be combined in any technically possible way.

A method and apparatus comprising improving the presentation of information to a user is disclosed. This is accomplished through an app or webpage, which is can be called my site. This method involves segmenting presented information on display into discrete items. An artificial intelligence algorithm categorizes the items. For example, the categories could be "of interest" and "of non-interest" to a user. Passive or active feedback is used to train the AI algorithm over time. Thus, the AI learns which items are of interest and which items are of non-interest and over time, the personalized app can present more relevant and personalized information. There are two improvements over the current processes.

First, the data is presented to the user in a consistent format. If a user wants to look at the FoxNews.com webpage, he/she will have to learn how to navigate through this page. If a user wants to look at the CNN.com webpage, he/she will have to learn how to navigate through this page. Learning how to navigate a number of different webpages takes time and energy.

Second, much of the data on a webpage is of non-interest to a given user. For example, FoxNews.com may have a featured article that the stock market has dropped 7% in a single trading day, but that piece of information may be of non-interest to a particular user. Additionally, a website may be filled with unwanted advertisements.

The personalized webpage overcomes both of these difficulties by presenting the information in a consistent format tailored to an individual user. For example, a user can select features including, but not limited to, the following: font size; layout of webpage; and, background of webpage. Additionally, the personalized webpage displays items of interest only. Specifically, items of non-interest are filtered. Thus, the personalized webpage improves presentation of information.

In some embodiments, items of non-interest are covered by a dynamic content blocking image. In other embodiments, items are filtered and a new webpage is generated, which looks similar to the parent webpage, but items are resized and moved (e.g., in position or in orientation). Still in other embodiments, a composite, personalized webpage with content extracted from at least two sources is performed. Such personalized webpage can be designed to satisfy the user. Still in other embodiments, personalized secondary notifications (e.g., sounds, visual notifications such as digital objects, and haptic feedback) can supplement the newly displayed items on the personalized webpage. Still in other embodiments, AI filtering of applications can be performed, so as to limit the information overload, and display the "of interest" items to the user on the personalized my site application/website. Finally, the my site application will have an AI driven psychological boost feature by assigning characteristics to a AI person who can serve many roles: friend; coach; counselor; teacher; or, even a grandmother of the user.

Still other embodiments include a computerized device, configured to process all the method operations disclosed herein as embodiments of the invention. In such embodiments, the computerized device includes a memory system, a processor, communications interface in an interconnection mechanism connecting these components. The memory system is encoded with a process that provides steps explained herein that when performed (e.g. when executing) on the processor, operates as explained herein within the computerized device to perform all of the method embodiments and operations explained herein as embodiments of the invention. Thus any computerized device that performs or is programmed to perform processing explained herein is an embodiment of the invention.

Other arrangements of embodiments of the invention that are disclosed herein include Software programs to perform the method embodiment steps and operations Summarized above and disclosed in detail below. More particularly, a computer program product is one embodiment that has a computer-readable medium including computer program logic encoded thereon that when performed in a computerized device provides associated operations providing steps as explained herein.

The computer program logic, when executed on at least one processor with a computing system, causes the processor to perform the operations (e.g., the methods) indicated herein as embodiments of the invention. Such arrangements of the invention are typically provided as Software, code and/or other data structures arranged or encoded on a computer readable medium such as an optical medium (e.g., CD-ROM), floppy or hard disk or other a medium such as firmware or microcode in one or more ROM or RAM or PROM chips or as an Application Specific Integrated Circuit (ASIC) or as downloadable software images in one or more modules, shared libraries, etc. The software or firmware or other Such configurations can be installed onto a computerized device to cause one or more processors in the computerized device to perform the techniques explained herein as embodiments of the invention. Software processes that operate in a collection of computerized devices, such as in a group of data communications devices or other entities can also provide the system of the invention. The system of the invention can be distributed between many software processes on several data communications devices, or all processes could run on a small set of dedicated computers, or on one computer alone.

It is to be understood that the embodiments of the invention can be embodied strictly as a software program, as Software and hardware, or as hardware and/or circuitry alone. Such as within a data communications device. The features of the invention, as explained herein, may be employed in data processing devices and/or Software systems for Such devices. Note that each of the different features, techniques, configurations, etc. discussed in this disclosure can be executed independently or in combination. Accordingly, the present invention can be embodied and viewed in many different ways. Also, note that this Summary section herein does not specify every embodiment and/or incrementally novel aspect of the present disclosure or claimed invention. Instead, this Summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF THE FIGURES

The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables, are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 5 illustrates types of data used to train the AI algorithm.

FIG. 6 illustrates types of categories for classification.

FIG. 9A illustrates a first time point of an image on a monitor wherein a segmented item of said image is classified as non-interest.

FIG. 9B illustrates a dynamic content blocker to be applied to the image at a first time point.

FIG. 9C illustrates a modified image at the first time point wherein an item on the image classified as non-interest is blocked by the dynamic content blocker.

FIG. 9D illustrates a second time point of an image on a monitor wherein a segmented item of said image is classified as non-interest.

FIG. 9E illustrates a dynamic content blocker to be applied to the image at a second time point.

FIG. 9F illustrates a modified image at the second time point wherein an item on the image classified as non-interest is blocked by the dynamic content blocker.

FIG. 18 illustrates secondary notifications relating informing user about displayed content.

FIG. 19 illustrates a table, which illustrates how classified content is determined to be displayed to a user.

FIG. 20 illustrates examples of artificial intelligence filtered applications.

DETAILED DESCRIPTION

Some aspects, features and implementations described herein may include machines such as computers, electronic components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

Figure 1A:
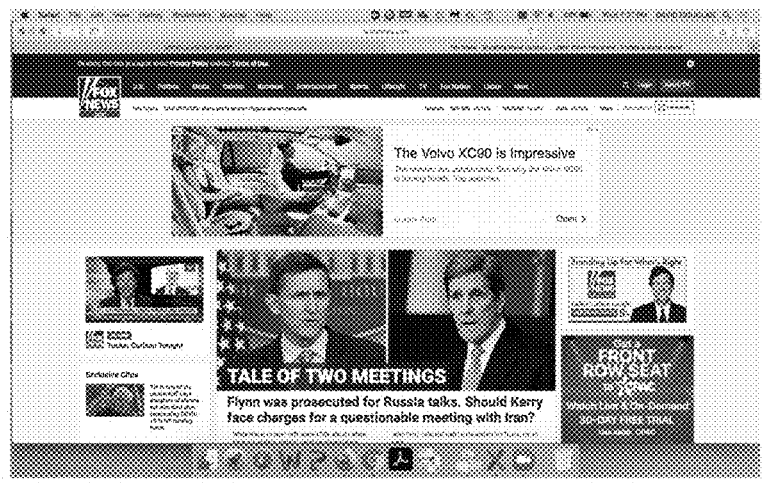
FIG. 1A illustrates prior art comprising an image displayed on a computer monitor at a first time point.

FIG. 1A illustrates prior art comprising an image displayed on a computer monitor at a first time point. Note various applications open on the desktop at the bottom of the image. Note that there are advertisements displayed on the webpage.

Figure 1B:
FIG. 1B illustrates prior art comprising an image displayed on a computer monitor at a second time point.

FIG. 1B illustrates prior art comprising an image displayed on a computer monitor at a second time point. Note at this second time point, a different portion of the webpage is shown. Note that the advertisements are located at different positions on the screen.

Figure 2:
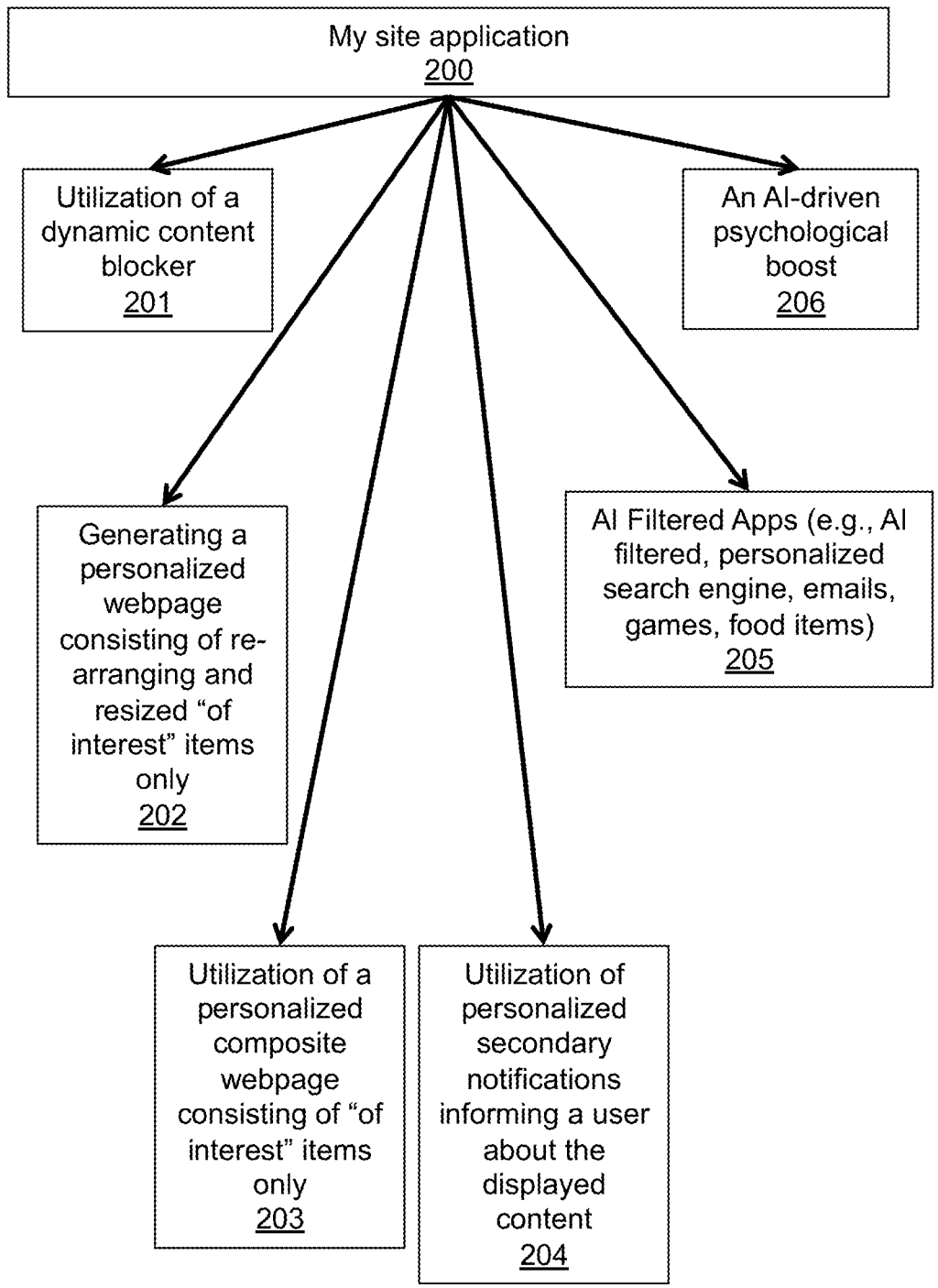
FIG. 2 illustrates the my site application overview.

FIG. 2 illustrates the my site application overview. 200 illustrates the my site application, which has several different features. 201 illustrates the feature of utilizing a dynamic content blocker. 202 illustrates the feature of generating a personalized webpage consisting of re-arranging and resized "of interest" items only. Alternatively, items can be changed in orientation. 203 illustrates the feature of utilizing a personalized composite webpage consisting of "of interest" items only. 204 illustrates the feature of utilizing personalized secondary notifications informing a user about the displayed content. 205 illustrates the feature of utilizing AI-filtered applications. 206 illustrates the feature of utilizing an AI driven psychological boost.

Figure 3:
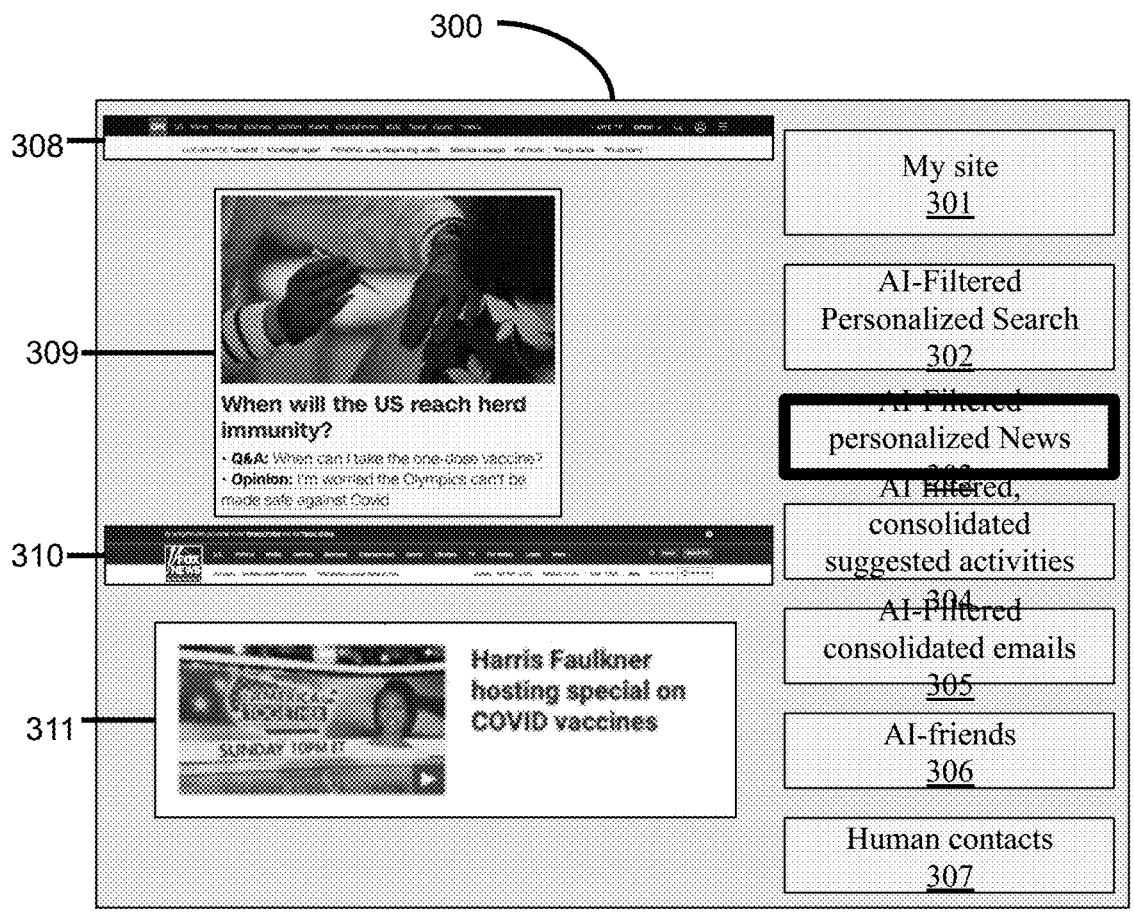
FIG. 3 illustrates an example homepage for the my site application/website home page.

FIG. 3 illustrates an example homepage for the my site application/website home page. This presentation of the my site application can be determined by the user or by an AI algorithm. In this example, the light blue background represents the user's preference. There are no advertisements and the my site application is clean appearing. An AI-filtered, personalized news can be utilized and shown in this home page 300. The novelty of the my site application is the performance of AI filtering so that the user is presented only "of interest" items. 301 illustrates the home button of the application. 302 illustrates the AI-filtered, personalized Internet search button. 303 illustrates the AI-filtered, personalized news button. For example, items from FoxNews.com and CNN.com can be analyzed by the AI and only "of interest" items are presented to the user. 304 illustrates the AI-filtered, consolidated suggested activities button. A user may have 40+ applications, many of which are suggesting activities to the user. This my site interface can use AI-filtering to generate suggested activities to the user. 305 illustrates the AI consolidated emails button. A user may have several email accounts including Hotmail, Outlook, Yahoo and Gmail. Learning each interface can be difficult. In this embodiment, AI filtering and presentation in a format that is well received by the user is performed. 306 illustrates the AI-friend button, which can serve to boost psychological health. 307 illustrates a human contact button, for applications such as texting or calling. 308 illustrates the CNN.com banner, which was deemed to be "of interest" by the AI algorithm and therefore imported into the my site application. 309 illustrates an article from CNN.com, which was deemed to be "of interest" by the AI algorithm and therefore imported into the my site application. 310 illustrates the FoxNews.com banner, which was deemed to be "of interest" by the AI algorithm and therefore imported into the my site application. 311 illustrates an article from FoxNews.com, which was deemed to be "of interest" by the AI algorithm and therefore imported into the my site application.

Figure 4:
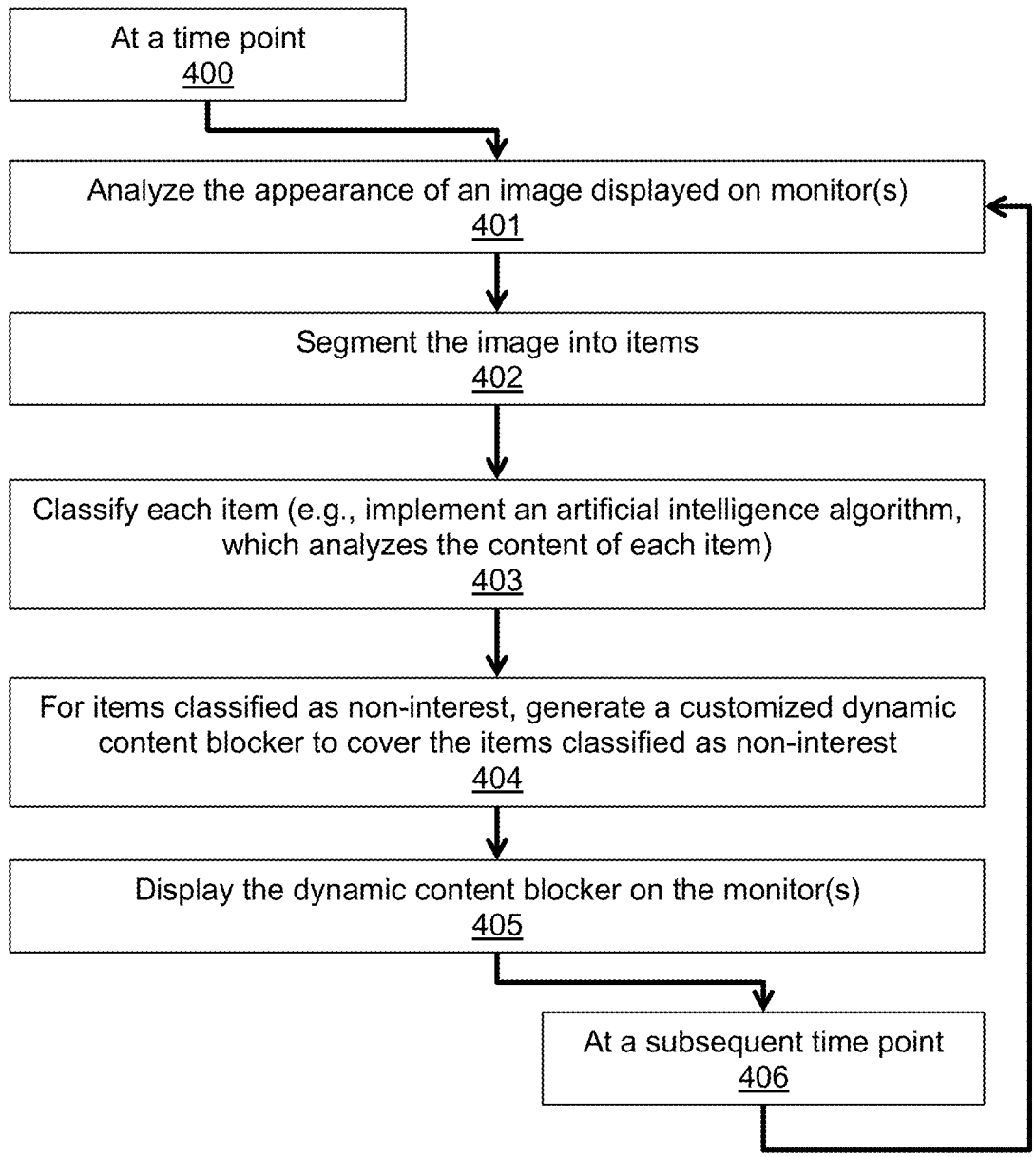
FIG. 4 illustrates an overview of the methodology of the dynamic content blocker.

FIG. 4 illustrates an overview of the methodology of the dynamic content blocker. The preferred embodiment is for a user's computer to run the dynamic content blocker app in the background and use the phone however he/she sees fit. The application will filter (hide) some of the content classified to be of non-interest, which is useful by reducing information overload to the user. This will improve the user's experience. For example, some advertisements may raise stress or not be appealing to a user. These such advertisements can be covered up by the dynamic content blocker. 400 illustrates a time point (e.g., a first time point). 401 illustrates a processing block comprising analyzing the appearance of an image displayed on monitor(s). _Software runs on computer and analyzes the appearance of the monitor(s). The monitor includes, but is not limited to the following: a desktop computer monitor; a laptop monitor; a TV; a smart phone; and, an extended reality displays (e.g., HoloLens 2). In some embodiments, it is envisioned that items of non-interest will be displayed as virtual objects within a 3D world. Items of non-interest in this embodiment could be filtered through processes taught in this patent. 402 illustrates a processing block comprising segmenting the image into items. 403 illustrates a processing block comprising classifying each item. For example, implement an artificial intelligence algorithm, which analyzes the content of each item. The artificial intelligence algorithm can learn from feedback from a user. For example, the user can input a hot key and draw a box over a displayed item of non-interest, so that it is hidden. This classification can be inputted into a training dataset, which is used to train the AI algorithm. The content can be the appearance of a picture, words or symbols within the segmented item. The items can be classified as "of interest" or "of non-interest". A certainty level can also be implemented, which can be used to drive the appearance of the dynamic content blocker. For example, if an item is classified as greater than or equal to 90% certainty that the item is "of non-interest", then a dynamic content blocker can be generated for this item. If, however, the item is classified as less than or equal to 89% certainty that the item is "of non-interest", then the dynamic content blocker is not generated for this item. 404 illustrates a processing block comprising for items classified as non-interest, generate a customized dynamic content blocker to cover the items classified as non-interest. 405 illustrates a processing block comprising display the dynamic content blocker on the monitor(s). The appearance is discussed subsequently in this patent. 406 illustrates a subsequent time point. At the subsequent time point, return to processing block 401.

FIG. 5 illustrates types of data used to train the AI algorithm. The goal of this system is to optimize presentation of information to a user. To achieve this, it is absolutely essential to block (or filter) items of non-interest. It is also important to identify information that is predicted to be of interest to the user and make it noticeable by the user. Additionally, it is important to collect information from multiple sources. Custom pages are developed to maximize user appreciation. Finally, it is critical to have appropriate feedback to the AI algorithm. The goal of the feedback it to help improve classification into the "of interest" category and the "of non-interest" category. To achieve appropriate feedback, the user input must be classified along with the content.

With respect to user feedback, there are two types taught herein. First is active feedback from the user. This is where the user deliberately does something to train the AI. For example, the user clicks on a segmented item (with option to generate manual input of classification) to deliberately train the AI. This could be done via an "of interest" button or an "of non-interest" button. This could also be done via a "classification button" where the user assigns a classification to teach the AI why they classified it the way they did. For example, classifications buttons include, but are not limited to, the following: author; content; aesthetics of the image; time of day; and, others.

Second is passive feedback from user. This is where a camera can evaluate the user's facial expressions and the user's eye tracking. This can reveal gaze direction. For example, if the user studies an image with a pleasant appearance on the face, that can be used as an indicator of the "of interest" category. This could also be used to enhance psychological therapy. For example, if a particular sound or image were realized by eye tracking and facial expression analysis together to reduce stress, then these could be delivered in a strategic fashion. For example, if the person was yelling or stressed out, then the therapeutic images and sound could kick in. Additional passive feedback includes time spent reading the article. If the user reads the full article carefully, this can be an indicator of the "of interest" category. Additionally, whether the article was forwarded to a friend can also serve as passive feedback from the user and be used to train the AI algorithm. The AI algorithms could have personalities and voices. And there could be multiple. For example, a user could have 5 AI friends and say "Titan, show me what is going on". Titan is an AI algorithm who specializes in finances pertinent to the user and would display pertinent financial news. The user could say "Joey, I am feeling a bit stressed". Joey is an AI algorithm who loves puppies and wants to share videos and has a nice soothing voice. The user could say "Jack, I know I need to work out, but I don't have the motivation." Jack is a coach and would show the latest athletic news. The user could say "Katie, what is it going to be like outside today." Katie is an AI algorithm who loves the weather and brings up the weather and traffic news. The user could say "Olie, what is going on in the world". Olie is an AI algorithm that specializes in world news of interest to the user and the "of interest" world news can be populated on the app.

Additionally, the AI algorithm will need to classify the content to optimize the experience for the user. The content can be classified by image analysis. For example, the AI algorithm could learn that the user finds certain types of images "of interest" and other types of images "of non-interest". Other classification categories could also be utilized, which is discussed in image ##. The classification of the content includes, but is not limited to the following: image analysis; symbol analysis; semantic analysis; sound analysis; emoji analysis; and, text appearance analysis. For each group a variety of sub-groups can be used. For example, for semantic analysis, the word "mask" may be used for AI analysis. If the word "mask" is detected (e.g., through optical character recognition), then the article could be classified as COVID and delivered to User #1 in FIG. 14A.

FIG. 6 illustrates types of categories for classification. A range of categories can be used. For example, the user could use their app to search by category. For example, if the user wanted to read news just to see what is interesting, the user could search by the "of interest category" with the option to have AI determine which websites to look at or the option to check CNN and FoxNews and have the AI search from there and generate a composite webpage. In addition to the "of interest" search, the user could also perform the "of importance" search, the "makes happier" search, the "motivates" search, the "likely to be of interest to girlfriend" and the likely to be on bucket list" app. Binary classifications are shown to teach this concept. However, different variable types could also be used. For example, categorical variables, such as mild, moderate, severe.

Figure 7:
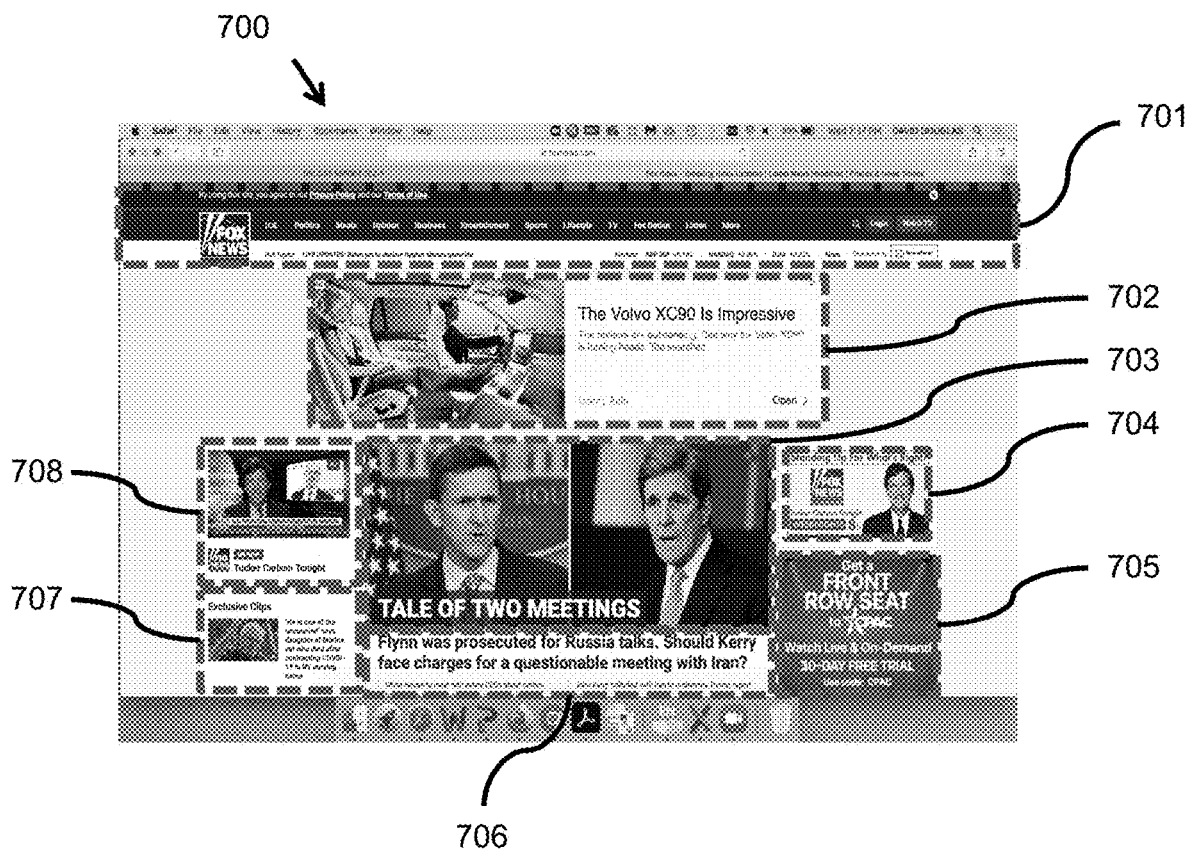
FIG. 7 illustrates segmentation of the image displayed on a computer monitor.

FIG. 7 illustrates segmentation of the image displayed on a computer monitor. A person who is of ordinary skill in the art could perform a variety of segmentation algorithms. 700 illustrates the image displayed on a computer monitor. 701 illustrates a first segmented item in the image 700. 702 illustrates a second segmented item in the image 700. 703 illustrates a third segmented item in the image 700. 704 illustrates a fourth segmented item in the image 700. 705 illustrates a fifth segmented item in the image 700. 706 illustrates a sixth segmented item in the image 700. 707 illustrates a seventh segmented item in the image 700. 708 illustrates the eighth segmented item in the image 700.

Figure 8:
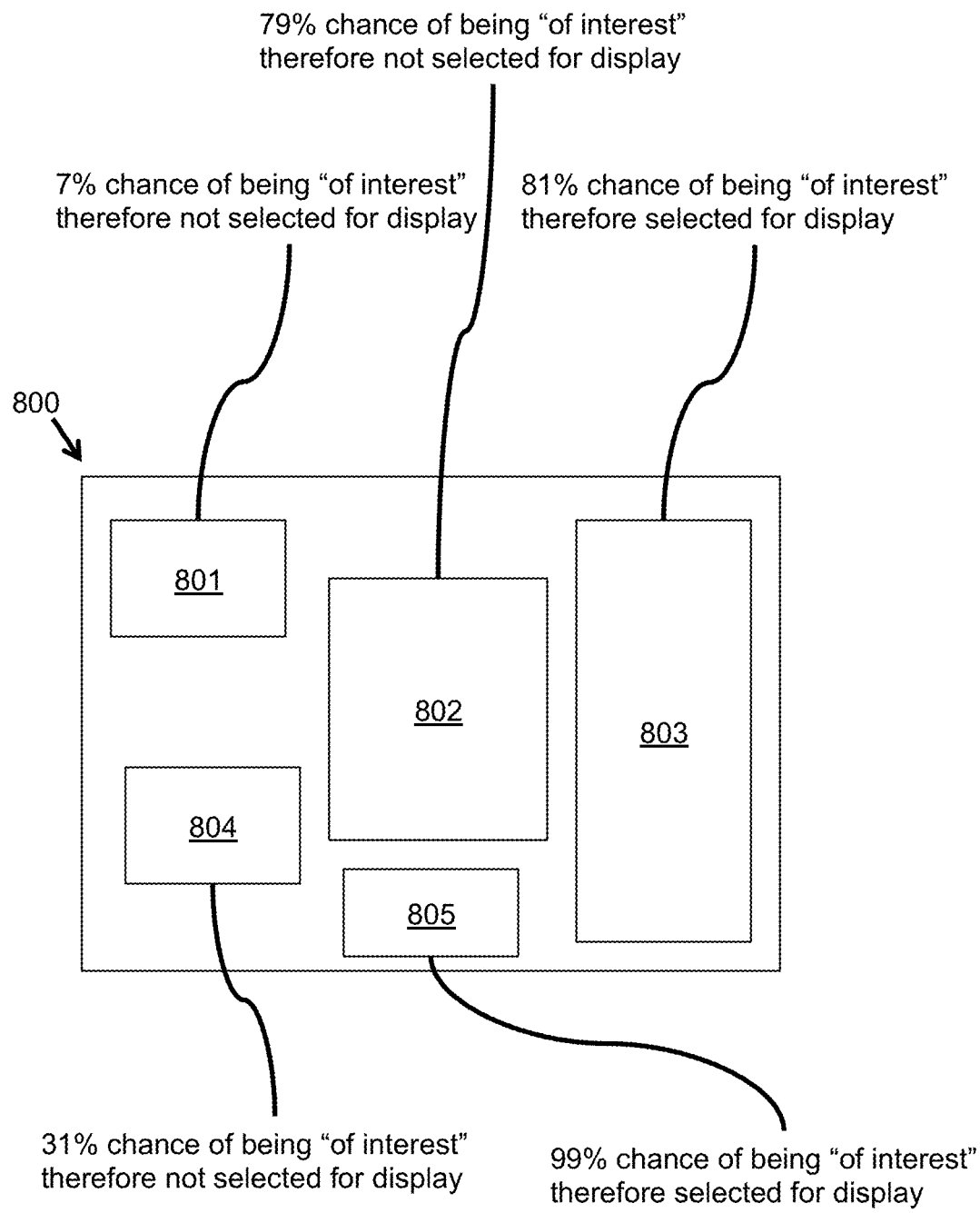
FIG. 8 illustrates using AI to determine which items to be displayed on my site.

FIG. 8 illustrates using AI to determine which items to be displayed on my site. Assume that the threshold is set at 80%. Therefore, if an item has an 80% chance or higher (predicted by AI) to be "of interest" to the user, it will be displayed on the my site application. If an item has lower than an 80% chance (predicted by AI) to be "of interest" to the user, then it will not be displayed on the my site application. 800 illustrates an image. 801 illustrates a first segmented item, which was determined by the AI algorithm to have a probability of being "of interest" of 7%. Therefore, item 801 is not selected for display on the my site app. 802 illustrates a second segmented item, which was determined by the AI algorithm to have a probability of being "of interest" of 79%. Therefore, item 802 is not selected for display on the my site app. 803 illustrates a third segmented item, which was determined by the AI algorithm to have a probability of being "of interest" of 81%. Therefore, item 803 is selected for display on the my site app. 804 illustrates a fourth segmented item, which was determined by the AI algorithm to have a probability of being "of interest" of 31%. Therefore, item 804 is not selected for display on the my site app. 805 illustrates a fifth segmented item, which was determined by the AI algorithm to have a probability of being "of interest" of 99%. Therefore, item 805 is selected for display on the my site app.

FIG. 9A illustrates a first time point of an image on a monitor wherein a segmented item of said image is classified as non-interest. 900 illustrates the image on the monitor. 901 illustrates an item in the image, which is classified as non-interest.

FIG. 9B illustrates a dynamic content blocker to be applied to the image at a first time point. 902 illustrates the border of the image on the monitor. 903 illustrates the dynamic content blocker to be applied to the image at the first time point.

FIG. 9C illustrates a modified image at the first time point wherein an item on the image classified as non-interest is blocked by the dynamic content blocker. 904 illustrates the modified image at the first time point wherein an item classified on the image as non-interest is blocked by the dynamic content blocker. 905 illustrates a black rectangle and the item is hidden from visibility.

FIG. 9D illustrates a second time point of an image on a monitor wherein a segmented item of said image is classified as non-interest. 906 illustrates the image on the monitor. 907 illustrates an item in the image, which is classified as non-interest. Note that this item (a different advertisement) is different from the item at the first time point.

FIG. 9E illustrates a dynamic content blocker to be applied to the image at a second time point. 908 illustrates the border of the image on the monitor. 909 illustrates the dynamic content blocker to be applied to the image at the second time point. Note that the dynamic content blocker has change in shape, size and location as compared to FIG. 9B. Also note that it can be changed in appearance.

FIG. 9F illustrates a modified image at the second time point wherein an item on the image classified as non-interest is blocked by the dynamic content blocker. 910 illustrates the modified image at the second time point wherein an item classified on the image as non-interest is blocked by the dynamic content blocker. 911 illustrates a black rectangle and the item is hidden from visibility. Additionally, the links behind the dynamic content blocker could be inaccessible.

Figure 10A:
FIG. 10A illustrates a image on a monitor wherein a segmented item of said image is classified as non-interest.

FIG. 10A illustrates a first time point of an image on a monitor wherein a segmented item of said image is classified as non-interest. 1000 illustrates the image on the monitor. 1001 illustrates an item in the image, which is segmented and classified as non-interest.

Figure 10D:
FIG. 10D illustrates the image in FIG. 10A with monitor a dynamic content blocker, which has a gray appearance with slight transparency.
Figure 10B:
FIG. 10B illustrates the image in FIG. 10A with monitor a dynamic content blocker, which has a white appearance.

FIG. 10B illustrates the image in FIG. 10A with monitor a dynamic content blocker, which has a white appearance. 1002 illustrates a modified image on the monitor, which is modified as compared to FIG. 10A. 1003 illustrates a dynamic content blocker, which has a white appearance, which hides the item of non-interest.

Figure 10E:
FIG. 10E illustrates the image in FIG. 10A with monitor a dynamic content blocker, which has a gray appearance with high transparency.
Figure 10C:
FIG. 10C illustrates the image in FIG. 10A with monitor a dynamic content blocker, which has a gray appearance.

FIG. 10C illustrates the image in FIG. 10A with monitor a dynamic content blocker, which has a gray appearance. 1004 illustrates a modified image on the monitor, which is modified as compared to FIG. 10A. 1005 illustrates a dynamic content blocker, which has a gray, non-transparent appearance, which hides the item of non-interest.

FIG. 10D illustrates the image in FIG. 10A with monitor a dynamic content blocker, which has a gray appearance with slight transparency. 1006 illustrates a modified image on the monitor, which is modified as compared to FIG. 10A. 1007 illustrates a dynamic content blocker, which has a gray, slightly transparent appearance, which hides the item of non-interest.

FIG. 10E illustrates the image in FIG. 10A with monitor a dynamic content blocker, which has a gray appearance with high transparency. 1008 illustrates a modified image on the monitor, which is modified as compared to FIG. 10A. 1009 illustrates a dynamic content blocker, which has a gray, highly transparent appearance, which hides the item of non-interest.

Figure 10F:
FIG. 10F illustrates the image in FIG. 10A with monitor a dynamic content blocker, which has an appearance to match the webpage's background.

FIG. 10F illustrates the image in FIG. 10A with monitor a dynamic content blocker, which has an appearance to match the webpage's background. 1010 illustrates a modified image on the monitor, which is modified as compared to FIG. 10A. 1011 illustrates a dynamic content blocker, which has a light gray appearance to match the webpage's background, which hides the item of non-interest. The example shown is of a 2D image on a 2D monitor. A wide range of image processing techniques can be used in conjunction with the dynamic content blocker. These techniques are discussed in the following patents and patent application disclosed herein.

These same taught techniques can also be applied to 3D images as displayed on head display units, which provide stereoscopic viewing on an extended reality display unit.

This is described in U.S. Pat. No. 8,384,771, METHOD AND APPARATUS FOR THREE DIMENSIONAL VIEWING OF IMAGES, which is incorporated by reference in its entirety. This patent teaches image processing techniques including volume generation, filtering, rotation, and zooming.

In some embodiments, stereoscopic viewing of the virtual 3D mannequin is performed with convergence, which is described in U.S. Pat. No. 9,349,183, METHOD AND APPARATUS FOR THREE DIMENSIONAL VIEWING OF IMAGES, which is incorporated by reference in its entirety. This patent teaches shifting of convergence. This feature can be used in combination with filtering.

In some embodiments, stereoscopic viewing can be performed using a display unit, which incorporates polarized lenses, which is described in U.S. Pat. No. 9,473,766, METHOD AND APPARATUS FOR THREE DIMENSIONAL VIEWING OF IMAGES, which is incorporated by reference in its entirety.

In some embodiments, advancements to display units can be incorporated for viewing the virtual 3D mannequin, which are taught in U.S. patent application Ser. No. 16/828,352, SMART GLASSES SYSTEM and U.S. patent application Ser. No. 16/997,830, ADVANCED HEAD DISPLAY UNIT FOR FIRE FIGHTERS, which are both incorporated by reference in their entirety.

In some embodiments, advancements in display units are taught in U.S. patent application Ser. No. 17/120,109, ENHANCED VOLUME VIEWING, which is incorporated by reference in its entirety. Included herein is a head display unit, which is improved by incorporating geo-registration.

Some embodiments comprise utilizing an improved field of view on an extended reality head display unit, which is taught in U.S. patent application Ser. No. 16/893,291, A METHOD AND APPARATUS FOR A HEAD DISPLAY UNIT WITH A MOVABLE HIGH RESOLUTION FIELD OF VIEW, which is incorporated by reference in its entirety.

In some embodiments, image processing steps can be performed using a 3D volume cursor, which is taught in U.S. Pat. No. 9,980,691, METHOD AND APPARATUS FOR THREE DIMENSIONAL VIEWING OF IMAGES, and U.S. Pat. No. 10,795,457, INTERACTIVE 3D CURSOR, both of which are incorporated by reference in its entirety.

In some embodiments, a precision sub-volume can be utilized in conjunction with the virtual 3D mannequin, which is taught in U.S. patent application Ser. No. 16/927,886, A METHOD AND APPARATUS FOR GENERATING A PRECISION SUB-VOLUME WITHIN THREE-DIMENSIONAL IMAGE DATASETS, which is incorporated by reference in its entirety.

In some embodiments, viewing of a structure at two different time points can be performed using a ghost imaging technique, which is taught in U.S. Pat. No. 10,864,043, INTERACTIVE PLACEMENT OF A 3D DIGITAL REPRESENTATION OF A SURGICAL DEVICE OR ANATOMIC FEATURE INTO A 3D RADIOLOGIC IMAGE FOR PRE-OPERATIVE PLANNING, which is incorporated by reference in its entirety.

Some embodiments comprise selecting a specific surgical device for pre-operative planning, which is taught in U.S. patent application Ser. No. 17/093,322, A METHOD OF SELECTING A SPECIFIC SURGICAL DEVICE FOR PREOPERATIVE PLANNING, which is incorporated by reference in its entirety.

Some embodiments comprise those taught in U.S. patent application Ser. No. 16/867,102, METHOD AND APPARATUS OF CREATING A COMPUTER-GENERATED PATIENT SPECIFIC IMAGE, which is incorporated by reference in its entirety. Key techniques include using patient factors (e.g., history, physical examination findings, etc.) to generate a volume.

Some embodiments comprise those taught in U.S. Pat. No. 10,586,400, PROCESSING 3D MEDICAL IMAGES TO ENHANCE VISUALIZATION, and U.S. Pat. No. 10,657,731, PROCESSING 3D MEDICAL IMAGES TO ENHANCE VISUALIZATION, both of which are incorporated by reference in its entirety.

Some embodiments comprise performing deformation techniques so that portions of the virtual 3D mannequin can be deformed and move in relation to other portions of the virtual 3D mannequin, which is taught in U.S. patent application Ser. No. 16/195,251, INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION, which is incorporated by reference in its entirety.

Some embodiments comprise those taught in U.S. patent application Ser. No. 16/736,731, RADIOLOGIST-ASSISTED MACHINE LEARNING WITH INTERACTIVE, VOLUME SUBTENDING 3D CURSOR, which is incorporated by reference in its entirety.

Some embodiments comprise wherein at least some component of the inserted 3D dataset into the virtual 3D mannequin are derived from cross-sectional imaging data fine-tuned with phantoms, which is taught in U.S. patent application Ser. No. 16/752,691, IMPROVING IMAGE QUALITY BY INCORPORATING DATA UNIT ASSURANCE MARKERS, which is incorporated by reference in its entirety.

Some embodiments comprise utilizing halo-type segmentation techniques, which are taught in U.S. patent application Ser. No. 16/785,606, IMPROVING IMAGE PROCESSING VIA A MODIFIED SEGMENTED STRUCTURE, which is incorporated by reference in its entirety.

Some embodiments comprise using techniques for advanced analysis of the virtual 3D mannequin taught in U.S. patent application Ser. No. 16/939,192, RADIOLOGIST ASSISTED MACHINE LEARNING, which are incorporated by reference in its entirety.

Some embodiments comprise performing smart localization from a first virtual 3D mannequin to a second virtual 3D mannequin, such as in an anatomy lab, which is performed via techniques taught in U.S. patent application Ser. No. 17/100,902, METHOD AND APPARATUS FOR AN IMPROVED LOCALIZER FOR 3D IMAGING, which is incorporated by reference in its entirety.

Some embodiments comprise performing a first imaging examination with a first level of mechanical compression and a second imaging examination with a second level of mechanical compression and analyzing differences therein, which is taught in U.S. patent application Ser. No. 16/594,139, METHOD AND APPARATUS FOR PERFORMING 3D IMAGING EXAMINATIONS OF A STRUCTURE UNDER DIFFERING CONFIGURATIONS AND ANALYZING MORPHOLOGIC CHANGES, which is incorporated by reference in its entirety.

Some embodiments comprise display using an optimized image refresh rate, which is taught in U.S. patent application Ser. No. 16/842,631, A SMART SCROLLING SYSTEM, which is incorporated by reference in its entirety.

Some embodiments comprise display using priority volume rendering, which is taught in U.S. Pat. No. 10,776,989, A METHOD AND APPARATUS FOR PRIORITIZED VOLUME RENDERING, which is incorporated by reference in its entirety.

Some embodiments comprise display using tandem volume rendering, which is taught in U.S. patent Ser. No. 17/033,892, A METHOD AND APPARATUS FOR TANDEM VOLUME RENDERING, which is incorporated by reference in its entirety.

Some embodiments comprise display using optimized fashion by incorporating eye tracking, which is taught in U.S. patent application Ser. No. 16/936,293, IMPROVING VISUALIZATION OF IMAGES VIA AN ENHANCED EYE TRACKING SYSTEM, which is incorporated by reference in its entirety.

Some embodiments comprise enhancing collaboration for analysis by incorporating teachings from U.S. patent application Ser. No. 17/072,350, OPTIMIZED IMAGING CONSULTING PROCESS FOR RARE IMAGING FINDINGS, which is incorporated by reference in its entirety.

Some embodiments comprise improving multi-user viewing of the virtual 3D mannequin by incorporating teachings from U.S. patent application Ser. No. 17/079,479, AN IMPROVED MULTI-USER EXTENDED REALITY VIEWING TECHNIQUE, which is incorporated by reference in its entirety.

Some embodiments comprise improving analysis of images through use of geo-registered tools, which is taught in U.S. Pat. No. 10,712,837, USING GEO-REGISTERED TOOLS TO MANIPULATE THREE-DIMENSIONAL MEDICAL IMAGES, which is incorporated by reference in its entirety.

Some embodiments comprise integration of virtual tools with geo-registered tools, which is taught in U.S. patent application Ser. No. 16/893,291, A METHOD AND APPARATUS FOR THE INTERACTION OF VIRTUAL TOOLS AND GEO-REGISTERED TOOLS, which is incorporated by reference in its entirety.

Some embodiments comprise those taught in U.S. patent application Ser. No. 16/506,073, A METHOD FOR ILLUSTRATING DIRECTION OF BLOOD FLOW VIA POINTERS, which is incorporated by reference in its entirety and U.S. Pat. No. 10,846,911, 3D IMAGING OF VIRTUAL FLUIDS AND VIRTUAL SOUNDS, which is also incorporated by reference in its entirety.

Some embodiments comprise those taught in U.S. patent Ser. No. 17/075,799, OPTIMIZING ANALYSIS OF A 3D PRINTED OBJECT THROUGH INTEGRATION OF GEO-REGISTERED VIRTUAL OBJECTS, which is incorporated by reference in its entirety.

Some embodiments also involve a 3D virtual hand, which can be geo-registered to the virtual 3D mannequin. Techniques herein are disclosed in U.S. patent application Ser. No. 17/113,062, A METHOD AND APPARATUS FOR A GEO-REGISTERED 3D VIRTUAL HAND, which is incorporated by reference in its entirety.

Some embodiments comprise those taught in U.S. patent application Ser. No. 16/654,047, METHOD TO MODIFY IMAGING PROTOCOLS IN REAL TIME THROUGH IMPLEMENTATION OF ARTIFICIAL, which is incorporated by reference in its entirety.

Some embodiments comprise those taught in U.S. patent application Ser. No. 16/597,910, METHOD OF CREATING AN ARTIFICIAL INTELLIGENCE GENERATED DIFFERENTIAL DIAGNOSIS AND MANAGEMENT RECOMMENDATION TOOL BOXES DURING MEDICAL PERSONNEL ANALYSIS AND REPORTING, which is incorporated by reference in its entirety.

Figure 11:
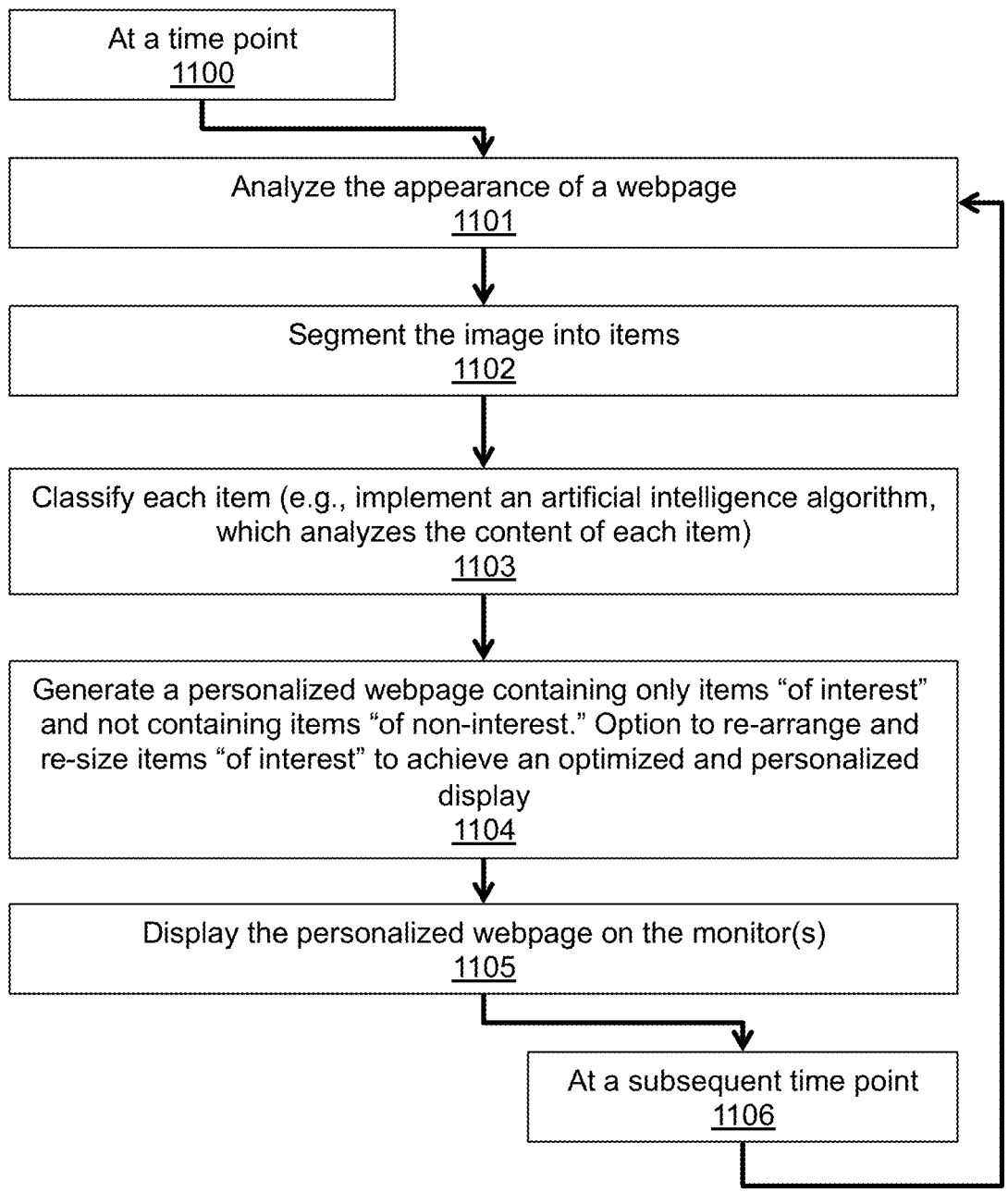
FIG. 11 illustrates an overview of the generating a personalized webpage consisting of re-arranging and resized "of interest" items only.

FIG. 11 illustrates an overview of the generating a personalized webpage consisting of re-arranging and resized "of interest" items only.

The preferred embodiment is for a user to view only items of interest on a given webpage during a browsing session. This will reduce stress from information overload and cause a more pleasing browsing experience. 1100 illustrates a time point (e.g., a first time point). 1101 illustrates a processing block comprising analyzing the appearance of a webpage (e.g., FoxNews.com). Software runs on computer and analyzes the appearance of the monitor(s). The monitor includes, but is not limited to the following: a desktop computer monitor; a laptop monitor; a TV; a smart phone; and, an extended reality displays (e.g., HoloLens 2). In some embodiments, it is envisioned that items of non-interest will be displayed as virtual objects within a 3D world. Items of non-interest in this embodiment could be filtered through processes taught in this patent. 1102 illustrates a processing block comprising segmenting the image into items. 1103 illustrates a processing block comprising classifying each item. For example, implement an artificial intelligence algorithm, which analyzes the content of each item. The artificial intelligence algorithm can learn from feedback from a user. For example, the user can input a "like" or a "dislike" on a segmented item that is presented to the user by the AI algorithm. This classification can be inputted into a training dataset, which is used to train the AI algorithm. The content can be the appearance of a picture, words or symbols within the segmented item. The items can be classified as "of interest" or "of non-interest". A certainty level can also be implemented. For example, if an item is classified as greater than or equal to 90% certainty that the item is "of interest", then item will be displayed on the personalized webpage. If this 90% threshold is not met, then the classified item will not be displayed on the personalized webpage. 1104 illustrates a processing block comprising generating a personalized webpage containing only items "of interest" and not containing items "of non-interest." 1105 illustrates a processing block comprising displaying the personalized webpage on the monitor(s). The appearance is discussed subsequently in this patent. 1106 illustrates a subsequent time point. At the subsequent time point, return to processing block 1101.

Figure 12A:
FIG. 12A illustrates segmentation of the image displayed on a computer monitor.

FIG. 12A illustrates segmentation of the image displayed on a computer monitor. 1200*a* illustrates a banner of FoxNews website. 1201*a* illustrates a first segmented item in the image. 1202*a* illustrates a second segmented item in the image. 1203*a* illustrates a third segmented item in the image. 1204*a* illustrates a fourth segmented item in the image. 1205*a* illustrates a fifth segmented item in the image. 1206*a* illustrates a sixth segmented item in the image. 1207*a* illustrates a seventh segmented item in the image.

Figure 12B:
FIG. 12B illustrates an example of the personalized webpage with filtering, re-arranging and resizing of components on the image.

FIG. 12B illustrates an example of the personalized webpage with filtering, re-arranging and resizing of components on the image. 1200*a* illustrates a banner of FoxNews.com website, which is not re-sized or rearranged. Note that 1201*a*, 1203*a* and 1204*a* have been filtered (subtracted or hidden) due to the AI algorithm determining that these items are of "non-interest". Note that 1202*b* illustrates the same image as 1202*a* in FIG. 12A, but it is now enlarged, and moved to a different position. Note that 1205*b* illustrates the same image as 1205*a* in FIG. 12A, but it is now enlarged, and moved to a different position. Note that 1206*b* illustrates the same image as 1206*a* in FIG. 12A, but it is now enlarged, and moved to a different position. Note that 1207*b* illustrates the same image as 1207*a* in FIG. 12A, but it is now enlarged, and moved to a different position. Thus, it does not matter what visual items of non-interest Foxnews.com website displays, using this app will allow filtering and re-arranging to maximize the individual user's experience.

Figure 13:
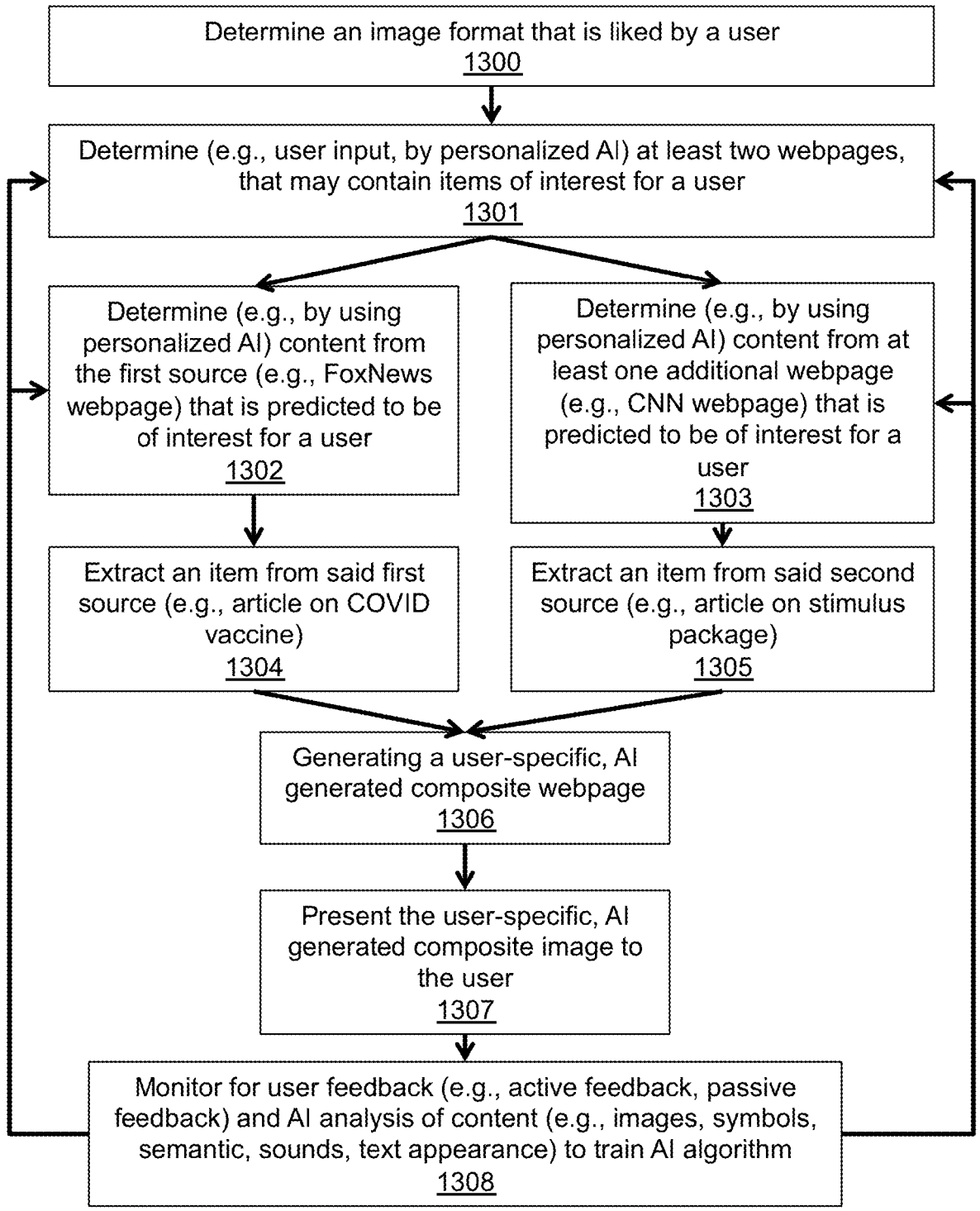
FIG. 13 illustrates the generation of an AI generated composite image of at least two webpages.

FIG. 13 illustrates the generation of an AI generated composite image of at least two webpages. 1300 illustrates a processing block comprising determining an image format that is liked by a user. This could take the form of a dynamic personal webpage or an application. A variety of scenes, pictures, sounds, colors, happy verses, or other features as desired by the user. Alternatively, this image could also be blank for a clean feel. The image could be user generated by could be generated by an AI system. The image could change throughout the day. This software that executes this program could be running in the cloud or on the computer. 1301 illustrates a processing block comprising determining (e.g., user input, by personalized AI) at least two webpages that may contain items of interest for a user. For example, a user could go to the main personalized webpage and then select (e.g., click on check boxes) two or more webpages to browse. Alternatively, an AI algorithm can learn via collected patterns on the user as training data which websites the user typically views. For example, the user may regularly look at the weather first thing in the morning and the headlines of the local news to look for traffic patterns. The AI would learn this behavior over time and the user would go to a main user-specific app and the AI algorithm would already have learned what the user is prefers to be viewing (through machine learning, such as deep learning algorithms accompanied by the training data). The types of information presented in the composite image could be varied throughout the day. For example, one of the hot topics that a person may be interested in reading upon arriving to work each day is the status of the COVID vaccines and stimulus bill. The user may be interested in reading these if and only if the hot topics are on the main page of the news source (e.g., breaking news only). That would help the user's information be more similar to the general population. 1302 illustrates a processing block comprising determining (e.g., by using personalized AI) content from the first source (e.g., FoxNews webpage) that is predicted to be of interest for a user. 1303 illustrates a processing block comprising determining (e.g., by using personalized AI) content from at least one additional source (e.g., CNN webpage) that is predicted to be of interest for a user. 1304 illustrates a processing block comprising extracting an item or items from said first source (e.g., article on COVID vaccine). 1305 illustrates a processing block comprising extracting an item from said second source (e.g., article on stimulus package). 1306 illustrates a processing block comprising generating a user-specific, AI generated composite webpage. 1307 illustrates a processing block comprising presenting the user-specific, AI generated composite image to the user. This could be from any type of display, such as a smart phone, laptop, tablet or extended reality display. 1308 illustrates monitoring for user feedback (e.g., facial expression, reading the article) to train AI algorithm.

Figure 14A:
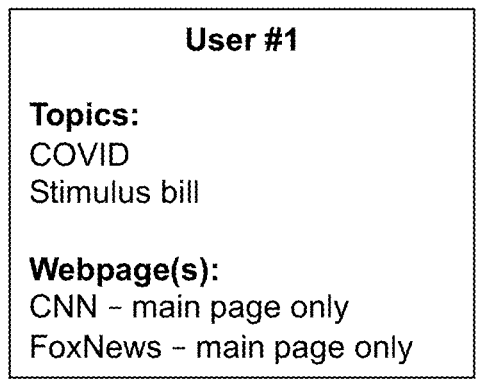
FIG. 14A illustrates a set of topics and webpages that the AI algorithm has learned that are "of interest" to user 1.

FIG. 14A illustrates a set of topics and webpages that the AI algorithm has learned that are "of interest" to user #1. With respect to topics, the AI algorithm has learned that "COVID" and "stimulus bill" articles should be classified as "of interest" for User #1. With respect to webpages, the AI algorithm has learned that the "CNN main page only" and "FoxNews main page only" articles should be classified as "of interest" for User #1. The AI algorithm will learn that these "of interest" items can be extracted and placed in a user-customized, personalized, dynamic webpage. It should be noted that User #1's personalized, dynamic webpage is illustrated in FIG. 15C.

Figure 14B:
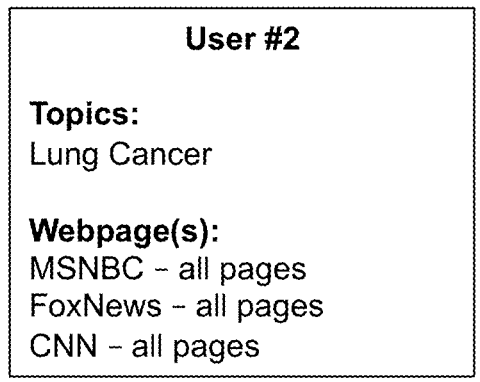
FIG. 14B illustrates a set of topics and webpages that the AI algorithm has learned that are "of interest" to user #2.

FIG. 14B illustrates a set of topics and webpages that the AI algorithm has learned that are "of interest" to user #2. With respect to topics, the AI algorithm has learned that "Lung Cancer" articles should be classified as "of interest" for User #2. With respect to webpages, the AI algorithm has learned that the entire "MSNBC" webpage, the entire "FoxNews" webpage and the entire "CNN" webpage articles should be classified as "of interest" for User #2.

Figure 14C:
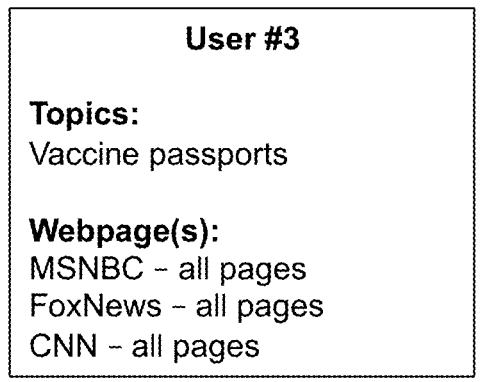
FIG. 14C illustrates a set of topics and webpages that the AI algorithm has learned that are "of interest" to user #3.

FIG. 14C illustrates a set of topics and webpages that the AI algorithm has learned that are "of interest" to user #3. With respect to topics, the AI algorithm has learned that "vaccine passport" articles should be classified as "of interest" for User #3. With respect to webpages, the AI algorithm has learned that the entire "MSNBC" webpage, the entire "FoxNews" webpage and the entire "CNN" webpage articles should be classified as "of interest" for User #3. Thus, the AI algorithm will learn that different users classify different items differently. In some embodiments, a user could share his/her profile to another user, so they could get a idea of their friend's interests and associated news profile.

Figure 15A:
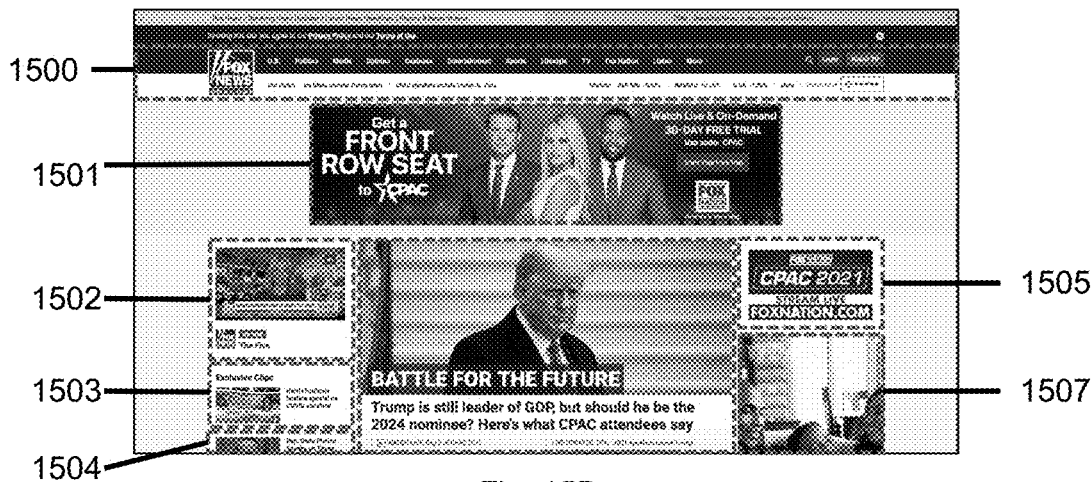
FIG. 15A illustrates a standard webpage, which in this example is FoxNews.com.

FIG. 15A illustrates a standard webpage, which in this example is FoxNews.com. 1500 illustrates a first segmented item on the FoxNews.com webpage, which is the banner with multiple buttons for navigation. This is categorized as "of interest". This can be done by a user because it is used for navigation on the composite personalized webpage. Alternatively, it can be done by an AI algorithm. 1501 illustrates a second segmented item on the FoxNews.com webpage, which is an advertisement for a 30-day free trial for a streaming. The AI categorizes this as "of non-interest". 1502 illustrates a third segmented item on the FoxNews.com webpage, which is an link to "The Five" show. The AI categorizes this as "of non-interest". 1503 illustrates a fourth segmented item on the FoxNews.com webpage, which is of Harris Faulkner hosting a special on COVID vaccines. The AI categorizes this as "of interest". The AI learns that the user seeks out new information on COVID. 1504 illustrates a fifth segmented item on the FoxNews.com webpage, which is of Rep. Dade Phelan speaking on Texas. The AI categorizes this as "of non-interest". 1505 illustrates a sixth segmented item on the FoxNews.com webpage, which is a link to FoxNation.com stream live. The AI categorizes this as "of non-interest". 1506 illustrates a seventh segmented item on the FoxNews.com webpage, which is a VRBO advertisement. The AI categorizes this as "of non-interest".

Figure 15B:
FIG. 15B illustrates a standard webpage, which in this example is CNN.com.
Figure 15C:
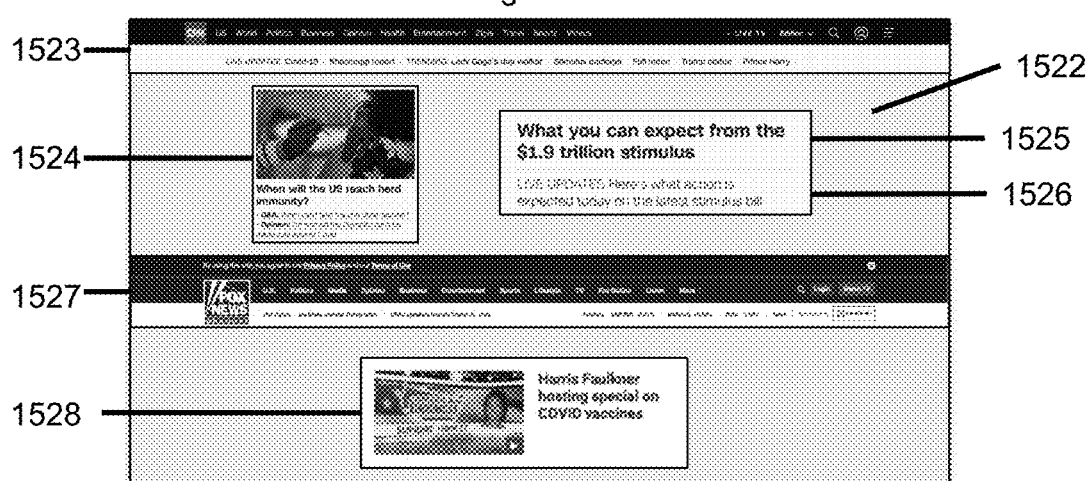
FIG. 15C illustrates a user-specific, AI generated composite webpage, which would correspond to User #1 in FIG. 14A.

FIG. 15B illustrates a standard webpage, which in this example is CNN.com. 1508 illustrates a first segmented item on the CNN.com webpage, which shows a video of a medical angiography room with a play button displayed. The AI categorizes this as "of non-interest". 1509 illustrates a second segmented item on the CNN.com webpage, which shows an advertisement for the Cleveland Clinic. The AI categorizes this as "of non-interest". 1510 illustrates a third segmented item on the CNN.com webpage, which shows two medical doctors wearing Cleveland Clinic white coats. The AI categorizes this as "of non-interest". 1511a illustrates a fourth segmented item on the CNN.com webpage, which is the general banner with multiple buttons for navigation. This is categorized as "of interest". This can be done by a user because it is used for navigation on the composite personalized webpage. Alternatively, it can be done by an AI algorithm. 1511b illustrates a fifth segmented item on the CNN.com webpage, which is the live updates banner with multiple buttons for navigation. This is categorized as "of interest". This can be done by a user because it is used for navigation on the composite personalized webpage. Alternatively, it can be done by an AI algorithm. 1512 illustrates a sixth segmented item on the CNN.com webpage, which is a featured article stating "Biden doesn't penalize Saudi Crown Prince". The AI categorizes this as "of non-interest". 1513 illustrates a seventh segmented item on the CNN.com webpage, which is a link, which states "What you can expect from the $1.9 trillion stimulus". The AI categorizes this as "of interest". 1514 illustrates a eighth segmented item on the CNN.com webpage, which is a link, which states "LIVE UPDATES Here's what action is expected today on the latest stimulus bill". The AI categorizes this as "of interest". 1515 illustrates a ninth segmented item on the CNN.com webpage, which is a link which states "Analysis: $1.9 trillion relief bill is a shockwave". The AI categorizes this as "of non-interest".

1516 illustrates a tenth segmented item on the CNN.com webpage, which is a link which states "Senate Democrats look for other ways to boost minimum wage after suffering setback". The AI categorizes this as "of non-interest". 1517 illustrates an eleventh segmented item on the CNN.com webpage, which is a link which states "Senate Democrats look for other ways to boost minimum wage after suffering setback". The AI categorizes this as "of non-interest". 1518 illustrates a twelfth segmented item on the CNN.com webpage, which is a link, which states that "Rand Paul slammed for grilling Biden's transgender health nominee". The AI categorizes this as "of non-interest". 1519 illustrates a thirteenth segmented item on the CNN.com webpage, which is a link which states "Analysis: Biden sends a message to Iran, but with a scalpel instead of a sledgehammer". The AI categorizes this as "of non-interest". 1520 illustrates a fourteenth segmented item on the CNN.com webpage, which is a link which states "When will the US reach herd immunity?". The AI categorizes this as "of interest". 1521 illustrates a fifteenth segmented item on the CNN.com webpage, which is an image stating "American Conservative Union". The AI categorizes this as "of non-interest".

FIG. 15C illustrates a user-specific, AI generated composite webpage, which would correspond to User #1 in FIG. 14A. 1522 illustrates the light blue background, which was user selected to be a soothing color. 1523 illustrates the CNN banner, which allows the user navigation of the CNN site, but using the user-specific, AI generated composite webpage as an interface. This obviates the need to look at the CNN webpage and the FoxNews webpage and then sort through numerous articles of non-interest; therefore, it is useful. It should be noted that the whole webpages can be analyzed and content classified as "of interest" or "of non-interest", not just a portion of the webpage. Thus, this also serves as an advantage and improvement over the prior art. 1524 illustrates the fourteenth segmented item on the CNN.com webpage, as shown in 1520 in FIG. 15B, which is a link which states "When will the US reach herd immunity?". Since the AI categorized this as "of interest", it is displayed on the user-specific, AI generated composite webpage. 1525 illustrates the seventh segmented item on the CNN.com webpage, as shown in 1513 in FIG. 15B, which is a link which states "What you can expect from the $1.9 trillion stimulus". Since the AI categorized this as "of interest", it is displayed on the user-specific, AI generated composite webpage. 1526 illustrates the eighth segmented item on the CNN.com webpage, as shown in 1514 in FIG. 15B, which is a link which states "LIVE UPDATES Here's what action is expected today on the latest stimulus bill". Since the AI categorized this as "of interest", it is displayed on the user-specific, AI generated composite webpage. Since items 1525 and 1526 are associated with one another, they are displayed together. 1527 illustrates the first segmented item on the FoxNews.com webpage, as shown in 1500 in FIG. 15A, which is the banner with multiple buttons for navigation. Since the AI categorized this as "of interest", it is displayed on the user-specific, AI generated composite webpage. 1528 illustrates the fourth segmented item on the FoxNews.com webpage, as shown in 1503 in FIG. 15A, which is of Harris Faulkner hosting a special on COVID vaccines. Since the AI categorized this as "of interest", it is displayed on the user-specific, AI generated composite webpage. In some embodiments, the user could sell space to advertisement agencies and get paid for having advertisement on their my site application.

FIG. 16A illustrates a process of modifying the personalized, composite webpage generated by an AI algorithm when a user clicks on a link on the personalized composite webpage. Processing block 1600 illustrates a user selects a link on composite page. In some embodiments, the AI could perform the selection of the link on the composite page. Processing block 1601 illustrates loading the source webpage, which corresponds to the link. Processing block 1602 illustrates running the AI analysis on the source webpage in processing block 1601 to determine items "of interest". Processing block 1603 illustrates generating new personalized, composite webpage or modify existing personalized composite page to include items of interest as determined by the AI in processing block 1602. Processing block 1604 illustrates displaying the new composite page or existing composite page.

Figure 17A:
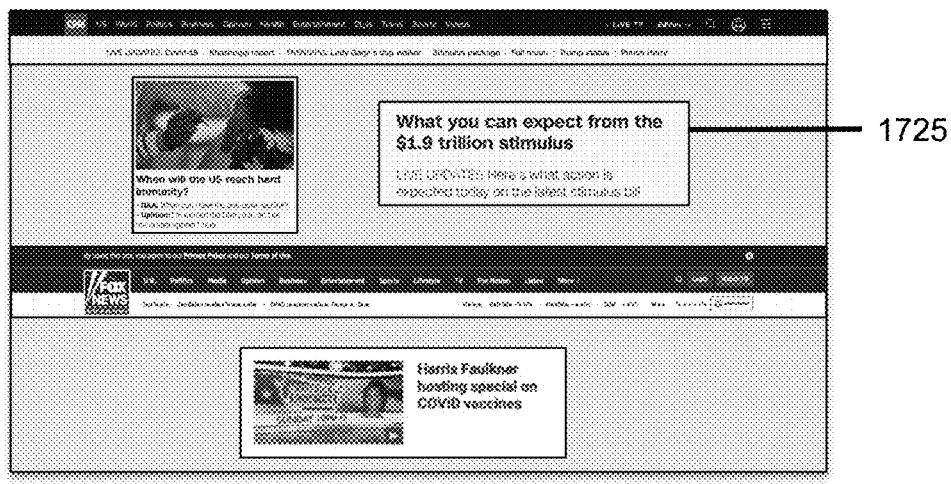
FIG. 17A illustrates the personal page, which in this situation is a composite user webpage.

FIG. 17A illustrates the personal page, which in this situation is a composite user webpage.

The personalized composite webpage, which contains the several items deemed by the AI algorithm to be of interest to the user. In this example, item 1725 is an article titled "what you can expect from the $1.9 trillion stimulus", which is clicked on by the user. The process in FIG. 14 is performed.

Figure 17B:
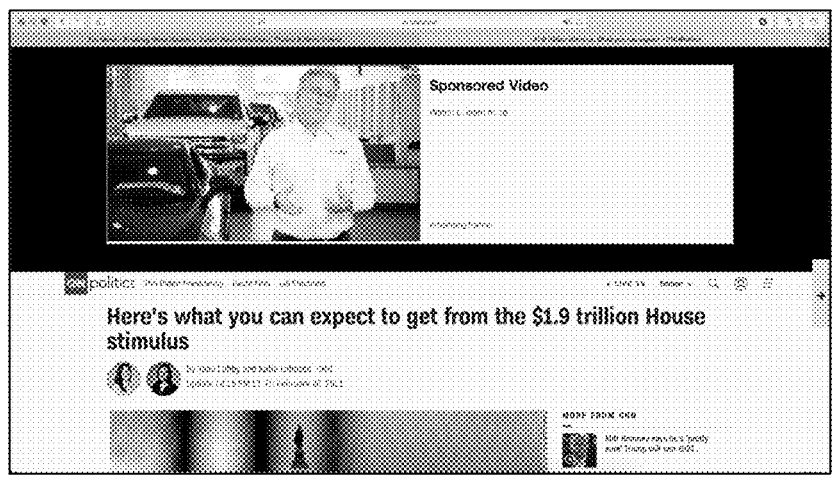
FIG. 17B illustrates the source of the link, which was activated on FIG. 17A.

FIG. 17B illustrates the source of the link, which was activated on FIG. 17A. In this patent, only items deemed by the AI algorithm deemed to be "of interest" are displayed to the user. The remaining items are not displayed to the user.

Figure 16:
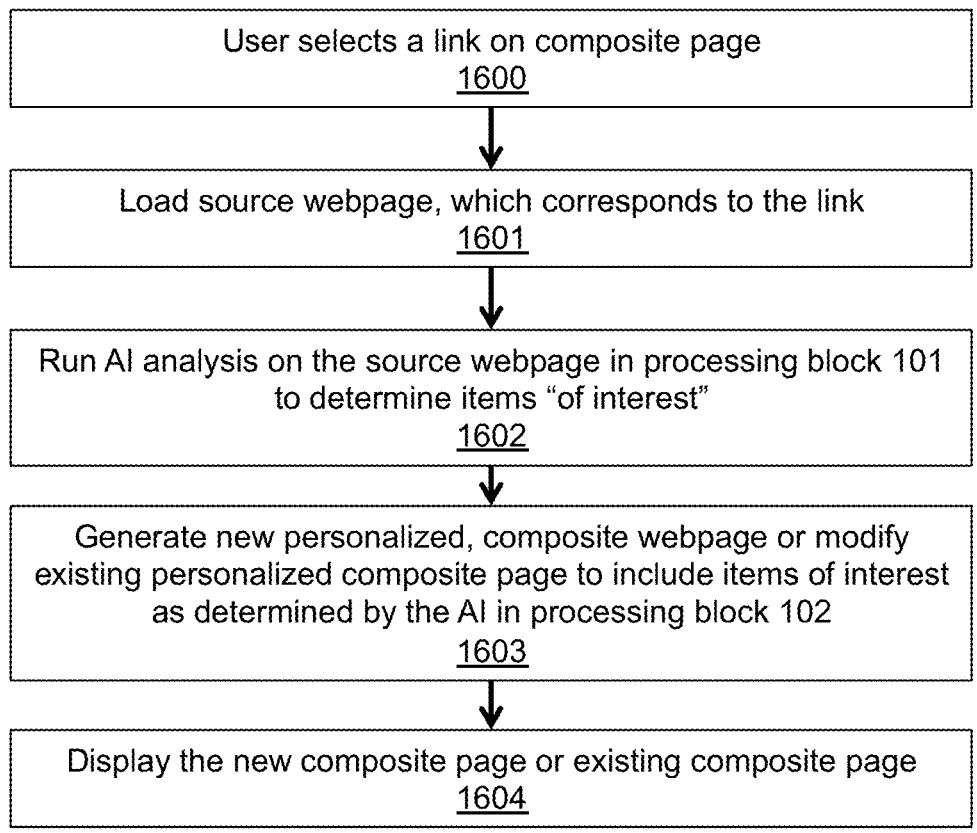
FIG. 16 illustrates a process of modifying the personalized, composite webpage generated by an AI algorithm when a user clicks on a link on the personalized composite webpage.
Figure 17C:
FIG. 17C illustrates the personalized, composite webpage, which in this situation shows the article selected in FIG. 17A.

FIG. 17C illustrates the personalized, composite webpage, which in this situation shows the article selected in FIG. 17A. Other content in the link shown in FIG. 17B are not displayed in the personalized, composite webpage. The process in FIG. 16 is performed. Thus, clicking on a link on the personalized composite webpage displays only "of interest" items from the link.

FIG. 18 illustrates secondary notifications relating informing user about displayed content. Processing block 1800 illustrates develop pre-determined criteria wherein predetermined criteria associates content classifications with notifications (sound(s), haptic feedback, visual notification (s)). For example, content in an item is classified as of high interest to a financial investment in a personal stock of a user is associated with a predetermined notification is a "ka-ching" sound. Content in an item is classified as a exciting sports related content is associated with a predetermined flash of a picture of a baseball over the item. Content in an item is classified as an exciting event that a user may want to participate in is associated with a haptic feedback notification. Processing block 1801 illustrates classifying content displayed on a monitor. Alternatively, classification of content on a portion of a monitor could be performed (e.g., a webpage). In some embodiments, a digital symbol can be shown while the program is active to indicate to the user that the image on the monitor is being analyzed, filtered and displayed with predetermined notifications. Processing block 1802 illustrates if classified content has an associated notification based on pre-determined criteria, then deliver the notification(s) to the user. For example, content is classified as being related to a personal stock of a user and a "ka-ching" sound is delivered to a user. Content is classified as a exciting sports and a flash of a picture of a baseball over the item is displayed to the user. Content is classified as an exciting event that a user may want to participate in and a haptic feedback notification is provided to the user. In some embodiments, the text on a webpage can be re-written with a preferred font style, color and size so as to accommodate those with poor eyesight.

FIG. 19 illustrates a table, which illustrates how classified content is determined to be displayed to a user. The first column is the classification of the content. The second column is filtering status. The third column indicates the predetermined notification. For example, in the first row, an item is classified by AI to be in the category of "sale of sporting equipment", which is filtered and no predetermined notification is provided. In the second row, an item is classified by AI to be in the category of the category of "news about COVID", which is not filtered (and therefore displayed to the user of the my site application) and no predetermined notification is provided. In the third row, an item is classified by AI to be in the category of "news about Tom Brady", which is not filtered because the AI algorithm has learned and classifies items on "Tom Brady" to be "of interest". Therefore, the AI algorithm does not filter the news about Tom Brady (and therefore displays the article to the user). A personalized pre-determined notification can be generated, such as a exciting, cheering sound from a stadium. In the fourth row, an item is classified by AI to be in the category of "sale at Talbots", which is filtered and no predetermined notification is provided. In the fifth row, an item is classified by AI to be in the category of "MBA recruitment", which is filtered and no predetermined notification is provided. In the sixth row, an item is classified by AI to be in the category of "precious metal advertisement", which is filtered and no predetermined notification is provided. In the seventh row, an item is classified by AI to be in the category of "scuba travel", which is filtered and no predetermined notification is provided.

In the preferred embodiment, the image displayed on a monitor is segmented into discrete items. Each segmented item is analyzed by an artificial intelligence (AI) algorithm. The AI algorithm performs classification of each segmented item. The classification is associated with a pre-determined filtering status and a pre-determined notification. In the preferred embodiment, both the filtering status (whether or not an item is filtered/subtracted) and the predetermined notification (sound, haptic feedback, visual feedback) are determined by the artificial intelligence algorithm. A user's inputs (e.g., data from eye tracking as taught in U.S. Ser. No. 16/683,256, A SMART SCROLLING SYSTEM, which is incorporated by reference in its entirety, data from user cursor clicks) are used to train the AI algorithm as to the filtering status and the predetermined notifications.

The AI filtering system can alleviate a tremendous amount of irritation and concomitant stress. By reducing the vast amount of advertisements, it can dramatically reduce the information overload, which in itself is highly stressful. In addition, it can also highlight advertisements or information that is of moderate to high interest. Overall, this decrease in irritation and only highlighting items of moderately to high interest can have an overall positive mental health effect.

In addition to filtering out those items of non-interest or irritation, the filtering system can also highlight only those items "of interest". This way those items of interest will not get buried amongst the non-interest items and will actually be showcased. In fact, these positive items of interest will be a source of happiness and not an irritant and cause stress. This can be done by filtering out items of non-interest and only showing items of interest. In addition to only showing these items of interest, there can be a auditory sound (e.g., jingle) that indicates an interested item. In fact, this jingle can be rated from "somewhat interested" to" highly interested "so as to alert the individual of the relative level of interest for each item. The jingle can be rated by each individual previously in order to indicate the level of interest. In the case of a change in the item of interest (new price, new features) it can have a separate jingle, if desired by the user. The volume can also be adjusted to indicate a level of importance to the individual. So if an person, for example, is waiting to hear about a merger, buy out opportunity etc. if can be highlighted by a loud jingle.

If, at any point in time, this process of perusing these items becomes stressful, the my site application/website the AI system will detect this and automatically reprioritize and decrease the number of hits. It can also showcase a previously identified scene of relaxation along with audio (e.g., sitting on the beach hearing the soothing sounds of the waves, sitting by a river with birds chirping, looking out at a lake). This AI feature can kick in whenever it senses an individual has reached their limit of frustration with advertisements and frankly with anything else.

FIG. 20 illustrates examples of artificial intelligence filtered applications. A user may have 40 or more applications on their phone. Many applications present extensive information to a user. Some of this information is of non-interest to the user. The my site application performs artificial intelligence filtering of information from the applications and then presents the information in a consistent format per user preference, as taught in this patent. A variety of applications can use the AI filtering technique as taught in this patent, including, but not limited to, the following: internet searches; e-mail; calendar events; games; directions; food delivery; and, dating applications.

Figure 21:
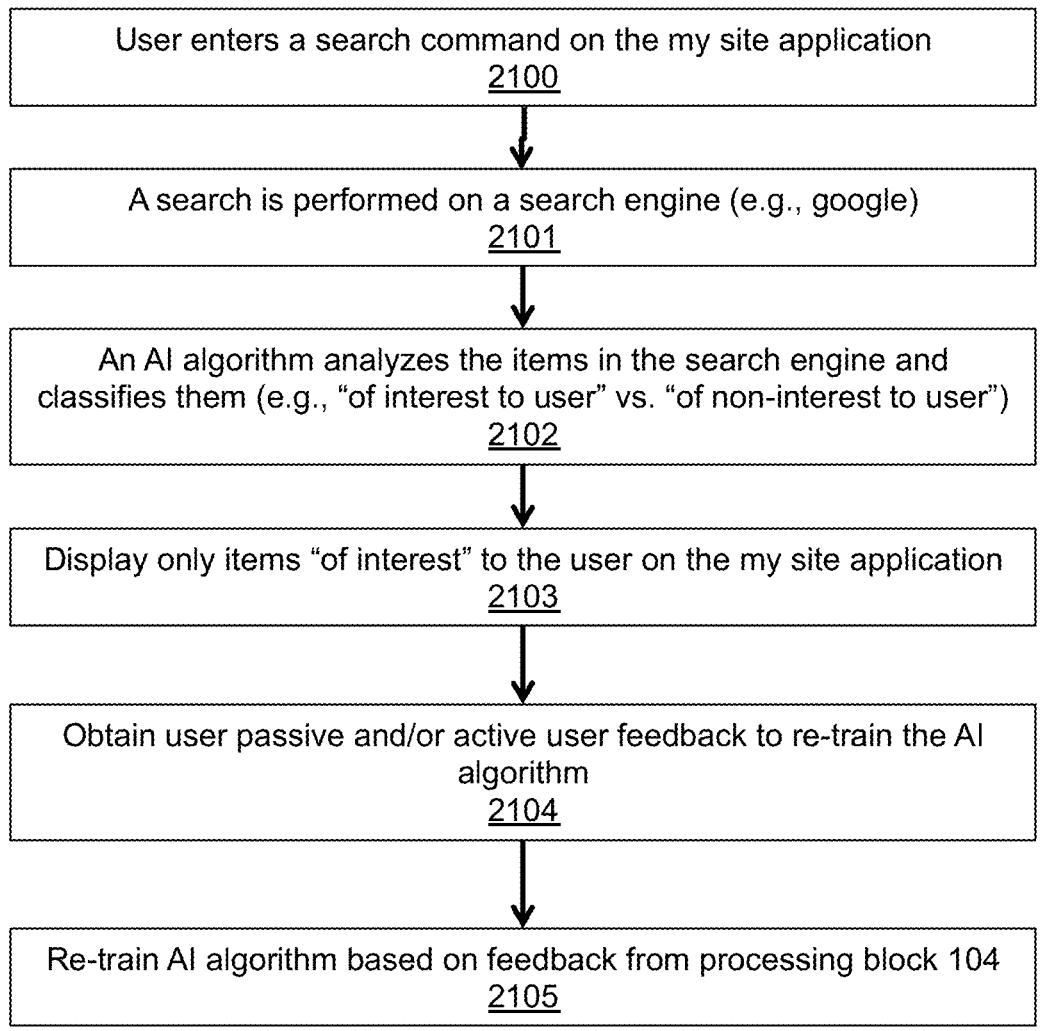
FIG. 21 illustrates a filtered, AI-personalized search.

FIG. 21 illustrates a filtered, AI-personalized search. Processing block 2100 illustrates a user entering a search command on the my site application. Processing block 2101 illustrates a search being performed on a search engine (e.g., google.com), which runs in the background. Processing block 2102 illustrates an AI algorithm specific to the user analyzes the items in the search engine and classifies them (e.g., "of interest to user" vs. "of non-interest to user"). Processing block 2103 illustrates displaying only items "of interest" to the user on the my site application. Processing block 2104 illustrates obtaining user passive and/or active user feedback to re-train the AI algorithm. Processing block 2105 illustrates re-training the AI algorithm based on feedback from processing block 2104.

Figure 22:
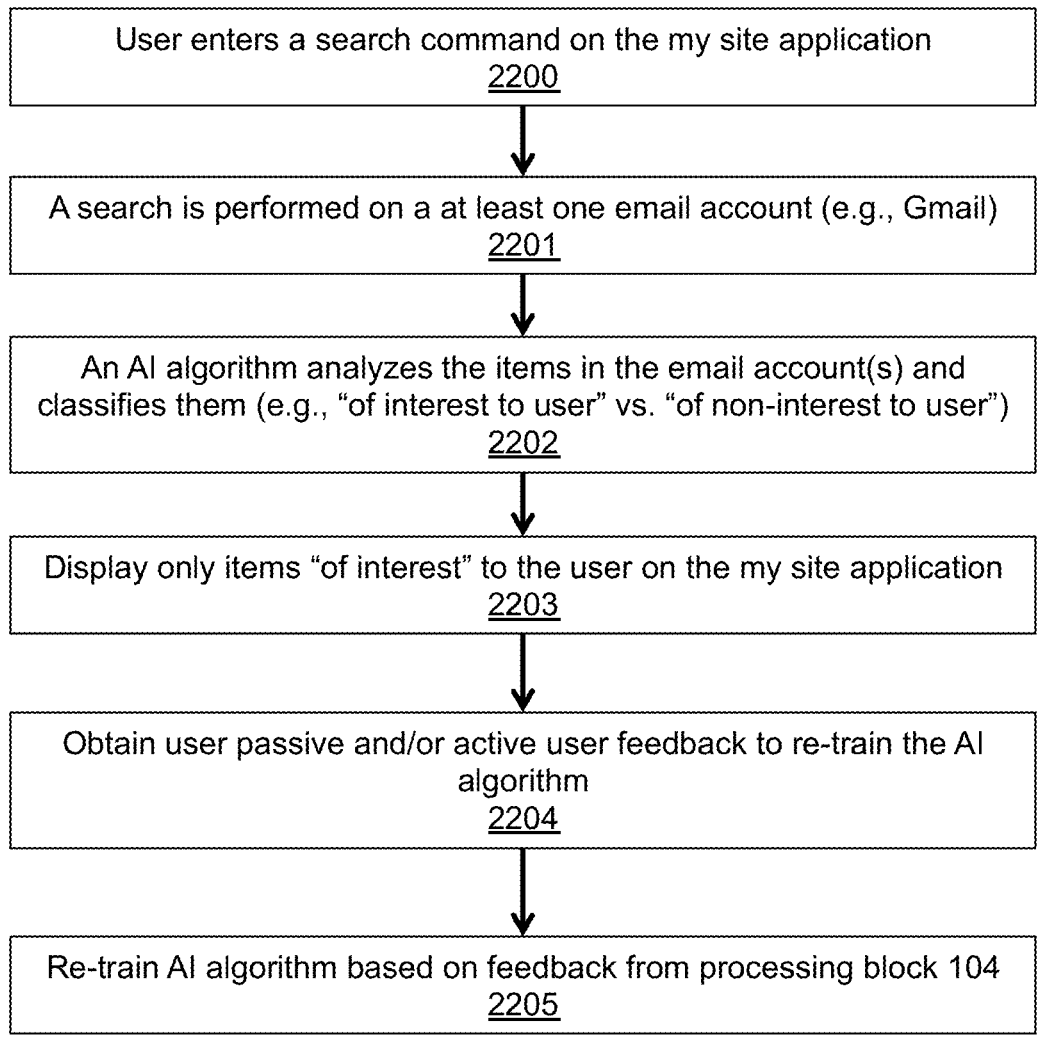
FIG. 22 illustrates a filtered, AI-personalized consolidation of email accounts.

FIG. 22 illustrates a filtered, AI-personalized consolidation of email accounts.

Processing block 2200 illustrates a user entering a search command on the my site application. Processing block 2201 illustrates a search is performed on a at least one email account (e.g., Gmail), which runs in the background. The Gmail application is not visualized by the user. Processing block 2202 illustrates an AI algorithm specific to the user analyzes the items in the email account(s) and classifies them (e.g., "of interest to user" vs. "of non-interest to user"). Processing block 2203 illustrates displaying only items "of interest" to the user on the my site application. Processing block 2204 illustrates obtaining user passive and/or active user feedback to re-train the AI algorithm. Processing block 2205 illustrates re-training the AI algorithm based on feedback from processing block 2204.

Figure 23:
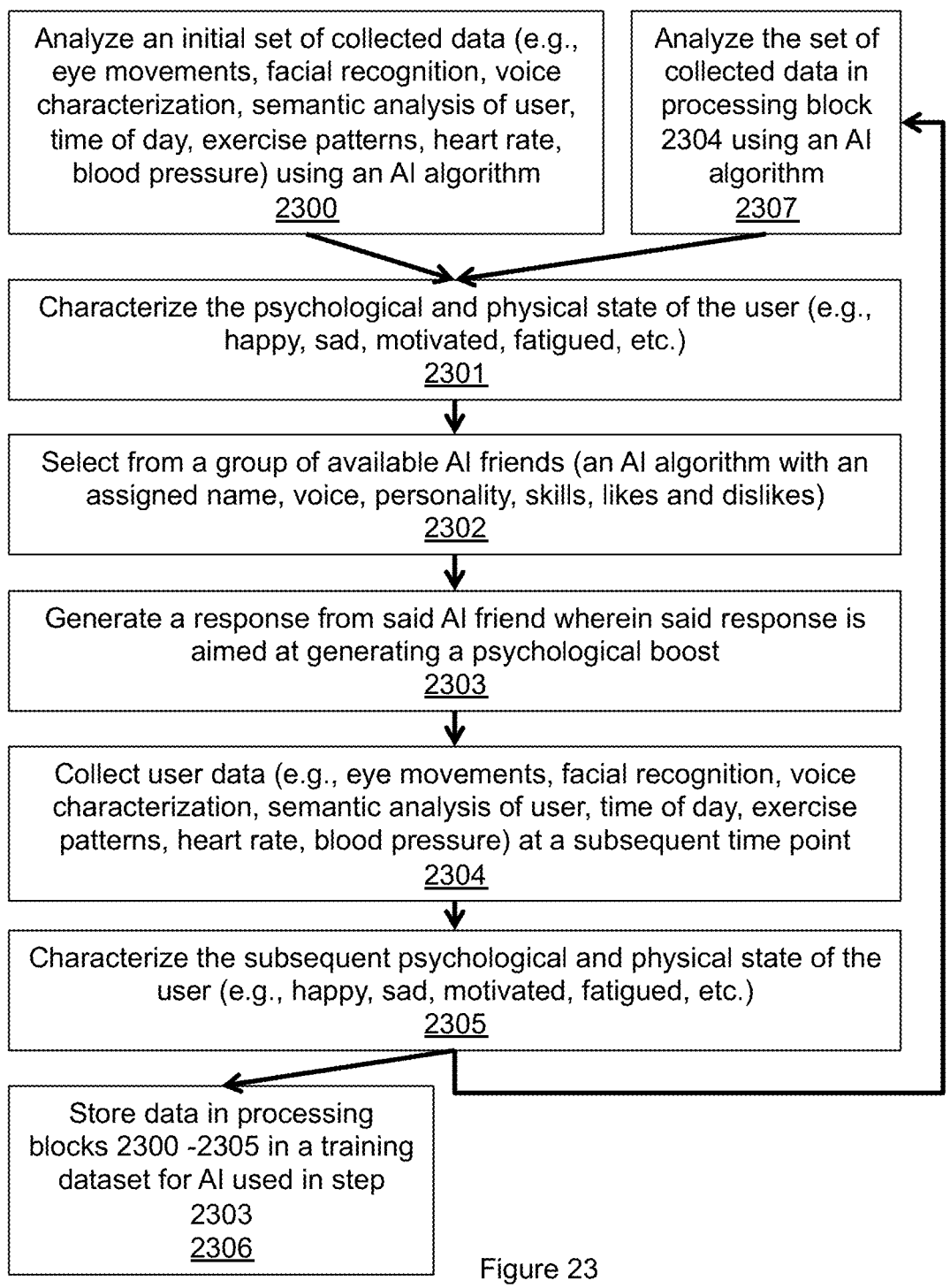
FIG. 23 illustrates utilizing information to enable a psychological boost for a user.

FIG. 23 illustrates utilizing information to enable a psychological boost for a user. Processing block 2300 illustrates analyzing an initial set of collected data (e.g., eye movements, facial recognition, voice characterization, semantic analysis of user, time of day, exercise patterns, heart rate, blood pressure) using an AI algorithm. Processing block 2301 illustrates characterizing the psychological and physical state of the user (e.g., happy, sad, motivated, fatigued, etc.). Processing block 2302 illustrates selecting from a group of available AI friends (an AI algorithm with an assigned name, voice, personality, skills, likes and dislikes). With respect to the processing block 2302, the AI friend could be a person who is known to the user, such as a grandmother. Processing block 2303 illustrates generating a response from said AI friend wherein said response is aimed at generating a psychological boost. Processing block 2304 illustrates collecting user data (e.g., eye movements, facial recognition, voice characterization, semantic analysis of user, time of day, exercise patterns, heart rate, blood pressure). Processing block 2305 illustrates characterizing the subsequent psychological and physical state of the user (e.g., happy, sad, motivated, fatigued, etc.) at a subsequent time point. Processing block 2306 illustrates storing data in processing blocks 2300-2305 in a training dataset so that the AI algorithm used in step 2303 can learn and improve over time. Processing block 2307 illustrates analyzing the set of collected data in processing block 2304 using an AI algorithm.

Figure 24:
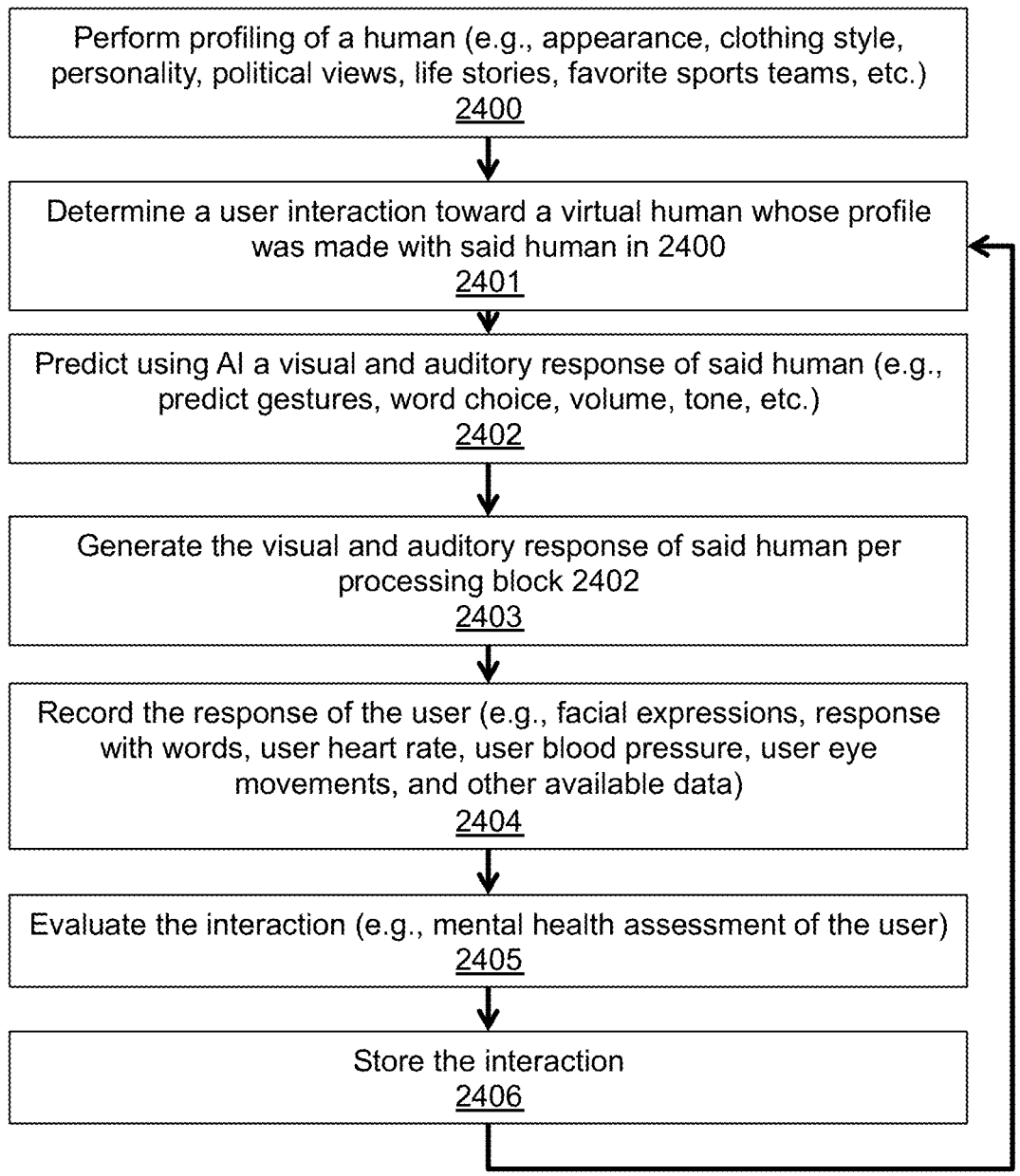
FIG. 24 illustrates achieving a psychological boost via a grandmother.

FIG. 24 illustrates achieving a psychological boost via a grandmother.

Throughout our lives we form very close ties with certain loved ones. Frequently, these special relationships provide us with a very supportive and safe space to share and talk through challenging decisions. We often rely on these special people to listen carefully and empathetically to our concerns and dilemmas and serve as a sounding board and perhaps even to offer confidential sage advice regarding decision-making. While the comfort from these special people in our lives is so important, when they are no longer with us, the grief from this loss can be devastating. Wouldn't it be a wonderful comfort to be able to communicate with a special loved one who has passed on? While we can still pray to them and ask them for guidance and prayers from the hereafter, it might also be a comfort to be able to actually speak to a virtual version of them (e.g., a "virtual grandmother) and hold a conversation with them like you once did. This embodiment provides a develop a simulated version of a loved one so that these former conversations could continue.

In addition to being able to speak to a virtual loved one and enjoy their feedback, conversations and advise, there may be other areas using this technology that can be helpful.

First, when remembering ones loved one such as a grandmother, there may be times when a person longs to say something to that loved one even though they have now passed on. Maybe, in such circumstances as the pandemic we are facing today, people have not had the chance to say a proper good-bye or say again how much they loved their special loved one. We all have moments when we wish we could go back and have said things differently. If we were given a chance to redo a conversation albeit virtually, it is possible this reenactment could perhaps provide a sense of closure.

Additionally, there may be other opportunities to redo conversations or difficult exchanges. As an examples, perhaps one wished that their parent told them that they were proud of them, but somehow they never did. This longing and disappointment may have left a real void and hurt. Perhaps a redo in the exchange with this parent where they said how much they were proud of a person albeit a virtual experience would be helpful to healing some hurts and wounds. People would then at least realize that had those important words been said in a different universe they would be happier.

Additionally, there may be still other personal exchanges that a person wished that they had handled differently. Perhaps they were not sensitive to the other person and were not as kind as they might have intended. They might want a chance to learn from an unsatisfactory exchange and practice a new strategy and then realize how this new strategy of alternative comebacks is far more satisfying. Or perhaps they were not assertive enough and regretted not standing up for themselves and then had the chance to try out alternative comebacks and see virtually how much better they felt. These corrective emotional experiences can be helpful to our mental well being but, can also illuminate and teach us better ways to converse during problematic conversations in the future. Practicing alternative communication with virtual exchanges with associated AI feedback can be very helpful in adopting improved strategies. Or if someone has anger issues, they can see how hurtful these behaviors are to others. Virtual training to help curtail anger and replace it with more polite and caring responses can also be practiced virtually. The individual will see the reactions from the other person generated by AI when different behaviors are demonstrated and with practice these will become the automatic responses.

This figure illustrates several processing blocks to perform the simulated encounter with the virtual human. For the purpose of teaching this invention we shall call this person Grandmother (GM). This term is equally applicable to a real grandfather, uncle, brother/sister, or other persons. While the person is alive, encounters with the simulated loved one could be performed and tested to see how realistic conversation and interactions appeared and updates could be made as needed. An apparatus, a process and software intended to capture the essence of a real person for posterity's sake.

Processing block 2400 illustrates performing profiling of a human (e.g., appearance, clothing style, personality, political views, life stories, favorite sports teams, etc.). Many features of this person's life can be categorized and inputted into the profile. Features include, but are not limited to the following: physical appearance; dress appearance; personality profile; favorite stories; political views; favorite conversations; favorite sports teams; and, so on. With respect to physical appearance, a 3D map of the person or person's face could be performed (e.g., using LIDAR performed under a wide range of facial expressions including smiling and while talking and while talking). Additionally, video footage of the simulated person including voice, speech patterns, gait patterns, facial gestures will be recorded.

Numerous conversations with this loved one (phone and video) will be recorded. The person could be asked to discuss their opinions on many diverse issues as well as important values, beliefs and attitudes that have sustained them in life and they hold dear. They could also be asked to share and discuss a variety of topics such as their favorite memories, activities, books, sports, music, places in the world they have visited or wish they had and most admired role models as examples. After numerous video sessions, patterns of their facial expressions, speech patterns (including tone, tempo and word usage) voice patterns (including changes in volume that coincide with changes in affect and different conditions), frequency and patterns of laughter, types and patterns of gestures, body language (including overall posture as well as changes that occur when different topics and affect emerge). During these sessions, clothing and hairstyle patterns could be observed and ultimately replicated.

A series of assessments would be conducted. These would include various personality tests, which could be used to assess among other variables specific needs that the individual has not satisfied and is still striving to satisfy. This is important as it is the unsatisfied needs that direct much one of one's attention, motivation and behavior. Another personality test would involve assessing differences in the way people perceive and draw conclusions. Interests tests using Holland's instruments could establish an interest profile and concomitant personality types. An Intelligence tests could also be employed to measure one's reasoning ability and how well one uses information and logic to draw conclusions and forecast outcomes. Various aptitude measures could be considered as well. Profiles could be established based on the various measures and could be used to supplement the formation of an AI simulated version of the loved one. In addition to the aptitude tests and personality profile, interests, values and beliefs could also be assessed.

Processing block 2401 illustrates determining a user's interaction toward a said virtual human. To accomplish this, the user's facial expressions, tone, word choice, volume, hand gestures, eye contact can all be characterized. This data can be performed on a background of the user's natural state. For example, if the user is typically monotone in volume and becomes somewhat excited in their tone, this needs to be taken into account to fully appreciate the user's current communication with the virtual human. Additionally, just as the virtual human is characterized, so too should the user's personality profile, views, background, aptitude and other metrics as discussed in processing block 2401.

Processing block 2402 illustrates using AI to predict a visual and auditory response of said human (e.g., predict gestures, word choice, volume, tone, etc.). The large amount of training data acquired in processing block 2400 is critical in performing this.

Processing block 2403 illustrates generating the visual and auditory response of the GM per processing block 2402. The preferred embodiment is to display the virtual GM on a 3D stereoscopic extended reality headset or similar headset, which produces 3D visualization of imagery.

In the first implementation, creation of a 3D volume which, in turn, will be the basis for a virtual 3D GM. For example, consider using the process outlined in U.S. Pat. No. 8,384,771. There are multiple additional ways to create a 3D volume. For example, a volume can be created based on laser distance measurements from the laser source to different, closely spaced points on the surface of GM being measured, as performed in processing block 2400. These measurements could be taken with associated variations such as but not limited to the following: laser source position relative to the body taking measurements at multiple angles covering face, upper torso, or full body such that these collective laser measurements form a 3D volume; taken with scripted sequences such as; smile; frown; look concerned; look happy; laughing; etc.; GM read from prepared script and record movements of the mouth, and facial expression changes over time. In some implementations, a record of body measurements (e.g., height, width, depth over full range of body; differences in shoulder width with respect to the head, etc.) In further implementations, the laser points of focus could include variations of clothing such as on bare arms, bare arms with blouse/shirt; bare arms with sweater. Variations of clothing could also include but not be limited to: what one wears to a sporting event; a party, at home in casual attire. Based on these variations of the GM posture, a multiplicity of virtual 3D volumes would be created.

In the second implementation, videos would be created to obtain facial expressions, movement of the head and arms, etc., during various activities. These activities could include but not be limited to the following: taken with scripted facial sequences such as: smile; frown; blinking; look concerned; look happy; laughing; etc.; reading from a GM selected script; performing household duties; walking in a park; sitting/standing in various rooms of GM living location. In some implementations, interactive scenarios could be prepared and rehearsed so that changes in facial expressions over time to reflect GM's reactions to differing topics. In some implementations, mannerisms such as, but not limited to, how GM nods her head, laughs, actions of moving hand and arms would be video taped. In some implementations, during the recording of the videos, color would be used in the recording process for different skin tones. Based on the setting (s) there may be shadows and bright areas indicative of the effects of different lighting. Note that U.S. Pat. No. 8,384,771 allowed for voxels of different colors and shadings, so this can be used for rendering on the extended reality display. In some implementations, use different elements of wardrobe to encompass what GM would wear under differing outside/event conditions. For example, dress up for Thanksgiving dinner; going to 4$^{th}$ of July party; normal day at home for the different seasons. Note: these outer garments could correspond those garments used the above measurements. In further implementation of this videotaping, a careful review of coloring and proper shades would be performed such that the resulting 3D virtual GM closely matched that of the video taped GM.

In the third implementation, personality tests would be administered to GM These personality traits would subsequently be used in conjunction with artificial intelligence (AI) element to formulate GM responses during interactions with persons using the GM system. As an example, have each participant (i.e., GM (mandatory), expected high frequency users such as siblings, sons and daughters, grandchildren, key friends) to take the Myers Briggs (MB) personality test. Find out the general personality characteristics such as whether GM is an introvert or extravert, a person who is sensing or intuitive, thinking or feeling, and judging or perceiving. How does GM best interact with each of the personality categories? Next, are there any past interactions that would have a bearing on future GM interactions (e.g., with specific individuals, a past history of travel together, calamities that may have happened together, nicknames/ greeting between GM and other high likelihood users)? What are the relationships between GM and other high likelihood users and, importantly, the relationships between the various high likelihood users? What is meta data regarding high likelihood users such as but not limited to the following: birthdates/birthdays; educational history, work experience; and key interests. The AI element would also include a set of key phrases, which if used during an interaction, would trigger a response in facial expression of GM and also a change of mood (described in a subsequent implementation). In some implementations voice tone analysis could be utilized to better understand the actual emotional state of the person interacting with GM. For example, the person might say I'm OK but voice analysis might indicate the person is actually troubled. The personality tests, past interactions, relationships and meta data would be integrated into a coherent AI response/interactions package specific to GM. In some further implementations this would include development of a set of rules for interactions between GM and each of the high likelihood users.

In the next implementation, cause the 3D virtual volume of GM to transition in a natural way during the course of interactions. This would be accomplished through deformations of portions of the 3D volume created in the initial implementation using the processes described in U.S. Pat. Nos. 10,878,639 and 10,950,338. and also with directions provided by the AI element. For example, if GM was greeting one of the grandchildren, the AI element in conjunction with deformations would modify a normal the facial expressions to an expression of a smile and the corresponding voxels would change accordingly. In contrast, when AI element determines that there has been a cause for concern expressed by key words/phrases uttered by the person interacting with GM, the expression from normal to concerned look would take place through deformations. In further implementations, multiple interaction scenarios could be prepared for interactions between GM and each of the high likelihood users. The manner in which the voxel manipulation changed the normal expression could be compared with the video tapes taken in the second implementation. If discrepancies exist, the expression(s) would be altered accordingly.

In the next implementation, cause the 3D virtual volume of GM to be superimposed onto a virtual mannequin (i.e., the virtual GM would replace the corresponding elements of the virtual mannequin—head for head, hair for hair, arms and hands for arms and hands, and so on). In the first step in this implementation, the virtual mannequin would be modified (e.g., stretched or shrunk in accordance with GM's age group, body size and shape). Mannequin appendages such as arms and legs would be modified to correspond to measured appendages of GM. In some implementations, use different elements of GM's wardrobe to encompass what GM would wear under differing outside/event conditions would adorn the mannequin and its appendages.

In the next implementation, cause the 3D virtual volume of GM, which has now become the virtual GM mannequin to be able to employ articulations aspects. These articulations would include but are not limited to the following: head movements when nodding approval and when laughing; arms and hand movements when clapping or giving a 'high five'; performing household tasks; working on a GM hobby; walking in a park. (Note: the scope of these activities determined by those persons directing preparation of the virtual GM).

In the next implementation, cause the 3D virtual volume of GM, which has now become the virtual GM mannequin to interact with and respond to the commands of the AI element. The AI element would first, inter alia: evaluate the current situation between GM and the particular high likelihood including factors such as the situation at hand, mood of the interacting parties, particular setting during discussions. The AI element would next, inter alia: determine the appropriate GM response to include but be limited to the following: verbal response and tone of delivery; modifications, as required, in facial expressions; associated articulations of head and appendages. The AI element would next, inter alia: initiate the GM response including verbal, facial expressions with associated deformations, and associated mannequin articulations. Note that this is an ongoing sequences of queries and responses on the GM's part: ponder questions based on known situations; listen and evaluate the situation as it evolves during the interaction; prepare and deliver responses based on the interactions; update the memory property based on the interactions. The net result would be appropriate, timely interactions between GM and each of the high likelihood users.

In the next implementation, prepare interface dynamics with the intent that GM responds in an appropriate manner consistent with that of the Person Being Interacted With (PBIW). Examples include but are not limited to: 1) GM should try to match the mood of the PBIW: if the PBIW is happy, GM should be happy; if the PBIW is sad, likewise GM should be sad; if the PBIW is pensive, so should be GM; if the PWIB is concerned, GM should be also; and so on. 2) GM should be responsive to the attitude of the PBIW: if the PBIW is positive, GM should be positive also; if the PBIW has a negative attitude, GM may be positive as a means of encouragement. 3) GM should be responsive to the energy level of the PBIW: if the PBIW is apathetic, GM may be bright and cheerful.

In some implementations, the interactions will be built around a family and friends collectively watching in 3D, listening to and interacting with the virtual GM. GM could initially provide her background which could, inter alia, include: life in early, mid, and later life; schooling; ancestral linkages; key events over different stages of life; fun tales associated with the high likelihood family and friends attendees; a question and answer period.

In some embodiments, a diversity of locations for recording GM is performed. Sometimes in living room, kitchen, garden, park, etc. Sometimes in differing lighting conditions. Sometimes feedback into AI for initializing interactions is incorporated.

Some embodiments comprise setting a tone of GM appearance to match those in video to ensure authenticity of visuals. This will help achieve the best match of voxel tone with tone of corresponding video pixel Additionally, AI is important for interactions. AI response would take into account, inter alia, the factors cited in step 10, below.

Processing block 2404 illustrates recording the response of the user (e.g., facial expressions, response with words, user heart rate, user blood pressure, user eye movements, and other available data).

Processing block 2405 illustrates evaluating the interaction (e.g., mental health assessment, Processing blocks 2404 and 2405 are critical so that the AI can learn to modify reactions over time to continuously improve even after data in processing block 2400 is acquired.

Processing block 2406 illustrates storing the interaction.

In the next implementation, cause the 3D virtual volume of GM, which has now become the virtual GM mannequin to have a memory property integral to the response of the GM with each particular high likelihood user. This response is dynamic AI which would evolve over time based on factors such as but not limited to the following: last and previous interactions to formulate comprehensive understanding of user condition with respect to but, not limited to the following: friends; love life; job; health; financial status as of last interface. In some implementations, this information will be integrated into AI to formulate questions by GM of person interacted with such as: 'how is your friend X or Y'? How is you job with Company X going? You have a birthday coming in two weeks—what would you like for a present? As responses are received and new information is disclosed by person interacting with GM, the AI element is continuously updated. An update of the AI element will be performed upon conclusion of the interaction based of this latest interface.

Throughout the entirety of the present disclosure, use of the articles "a" or "an" to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, Something else, may be understood to so communicate, be associated with, and or be based on in a direct and/or indirect manner, unless otherwise stipulated herein. The device(s) or computer systems that integrate with the processor(s) may include, for example, a personal computer (s), workstation(s) (e.g., Sun, HP), personal digital assistant (s) (PDA(s)), handheld device(s) such as cellular telephone (s), laptop(s), handheld computer(s), or another device(s) capable of being integrated with a processor(s) that may operate as provided herein. Accordingly, the devices provided herein are not exhaustive and are provided for illustration and not limitation. References to "a microprocessor and "a processor, or "the microprocessor and "the processor." may be understood to include one or more microprocessors that may communicate in a stand-alone and/or a distributed environment(s), and may thus be configured to communicate via wired or wireless communications with other processors, where such one or more processor may be configured to operate on one or more processor-controlled devices that may be similar or different devices. Use of such "microprocessor or "processor terminology may thus also be understood to include a central processing unit, an arithmetic logic unit, an application-specific integrated circuit (IC), and/or a task engine, with such examples provided for illustration and not limitation. Furthermore, references to memory, unless otherwise specified, may include one or more processor-readable and accessible memory elements and/or components that may be internal to the processor-controlled device, external to the processor-controlled device, and/or may be accessed via a wired or wireless network using a variety of communications protocols, and unless otherwise specified, may be arranged to include a combination of external and internal memory devices, where Such memory may be contiguous and/or partitioned based on the application. Accordingly, references to a database may be understood to include one or more memory associations, where such references may include commercially available database products (e.g., SQL, Informix, Oracle) and also include proprietary databases, and may also include other structures for associating memory Such as links, queues, graphs, trees, with such structures provided for illustration and not limitation. References to a network, unless provided otherwise, may include one or more intranets and/or the Internet, as well as a virtual network. References hereinto microprocessor instructions or microprocessor-executable instructions, in accordance with the above, may be understood to include programmable hardware.

Unless otherwise stated, use of the word "substantially' may be construed to include a precise relationship, condition, arrangement, orientation, and/or other characteristic, and deviations thereof as understood by one of ordinary skill in the art, to the extent that such deviations do not materially affect the disclosed methods and systems. Throughout the entirety of the present disclosure, use of the articles "a" or "an" to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, Something else, may be understood to so communicate, be associated with, and or be based on in a direct and/or indirect manner, unless otherwise stipulated herein. Although the methods and systems have been described relative to a specific embodiment thereof, they are not so limited. Obviously many modifications and variations may become apparent in light of the above teachings. Many additional changes in the details, materials, and arrangement of parts, herein described and illustrated, may be made by those skilled in the art. Having described preferred embodiments of the invention it will now become apparent to those of ordinary skill in the art that other embodiments incorporating these concepts may be used. Additionally, the software included as part of the invention may be embodied in a computer program product that includes a computer useable medium. For example, such a computer usable medium can include a readable memory device, such as a hard drive device, a CD-ROM, a DVD ROM, or a computer diskette, having computer readable program code segments stored thereon. The computer readable medium can also include a communications link, either optical, wired, or wireless, having program code segments carried thereon as digital or analog signals. Accordingly, it is submitted that that the invention should not be limited to the described embodiments but rather should be limited only by the spirit and scope of the appended claims.

Several features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

What is claimed is:

1. A method comprising:
   generating a dynamic content blocker
   wherein said dynamic content blocker filters image content comprising at least one of image(s), picture(s), system(s), a word or text,
   wherein said dynamic content blocker comprises a blocker image that uses a filtering algorithm that changes over time points, and
   wherein at each time point in said time points,
   an analysis of said image content on a display is performed,
   wherein said image content contains item(s) of interest and item(s) of non-interest,
   wherein said analysis of said image content on said display evaluates for item(s) of non-interest to said user,
   wherein said analysis comprises an artificial intelligence algorithm for continued feedback, and
   wherein said artificial intelligence algorithm learns based on a user's facial expression upon a gaze at on items, and
   said blocker image is generated,
   wherein said blocker image is configured to cover said item(s) of non-interest; and
   displaying, at each time point in said time points, said dynamic content blocker and said image content on said display.

2. The method of claim 1 further comprising wherein said artificial intelligence algorithm learns based on said user feedback of items.

3. The method of claim 1 further comprising wherein said artificial intelligence algorithm learns based on an amount of time that said user spends on an item.

4. The method of claim 1 further comprising wherein said artificial intelligence algorithm learns based on whether the link is sent to another person.

5. The method of claim 1 further comprising wherein said dynamic content blocker has an appearance specified by a user.

6. The method of claim 1 further comprising wherein said dynamic content blocker has an appearance specified by an AI algorithm.

7. The method of claim 1 further comprising wherein said dynamic content blocker has an appearance of a homogeneous grayscale.

8. The method of claim 1 further comprising wherein said dynamic content blocker has an appearance specified by a homogeneous color.

9. The method of claim 1 further comprising wherein said dynamic content blocker has an appearance that matches the background of a webpage or an application.

10. The method of claim 1 further comprising moving at least one item of interest on said display.

11. The method of claim 1 further comprising changing the orientation of at least one item of interest on said display.

12. The method of claim 1 further comprising enlarging at least one item of interest on said display.

13. The method of claim 1 further comprising rearranging at least one item of interest.

14. The method of claim 1 further comprising causing links from items of non-interest to be inaccessible.

15. The method of claim 1 further comprising modifying the text of the items of interest.

16. The method of claim 1 further comprising displaying a predetermined notification to said user based on a classification of said content wherein said predetermined notification is a sound notification.

17. The method of claim 1 further comprising displaying a predetermined notification to said user based on a classification of said content wherein said predetermined notification is a haptic notification.

18. The method of claim 1 further comprising displaying a predetermined notification to said user based on a classification of said content wherein said predetermined notification is a visual notification.

* * * * *